United States Patent
Qi et al.

(10) Patent No.: US 7,118,215 B2
(45) Date of Patent: Oct. 10, 2006

(54) METHOD FOR DETERMINING OPTICAL VALUE OF LENS OF EYEGLASSES, PROCESS FOR PRODUCING LENS OF EYEGLASSES, LENS OF EYEGLASSES AND ITS ORDERING/ORDR RECEIVING SYSTEM

(75) Inventors: Hua Qi, Shinjuku-ku (JP); Takashi Hatanaka, Shinjuku-ku (JP)

(73) Assignee: HOYA Corporation, Tokyo (JP)

( * ) Notice: Subject to any disclaimer, the term of this patent is extended or adjusted under 35 U.S.C. 154(b) by 0 days.

(21) Appl. No.: 10/486,720

(22) PCT Filed: Oct. 7, 2003

(86) PCT No.: PCT/JP03/12820

§ 371 (c)(1),
(2), (4) Date: Feb. 23, 2004

(87) PCT Pub. No.: WO2004/034131

PCT Pub. Date: Apr. 22, 2004

(65) Prior Publication Data

US 2004/0257527 A1 Dec. 23, 2004

(30) Foreign Application Priority Data

Oct. 8, 2002 (JP) .............................. 2002-295315

(51) Int. Cl.
G02B 7/02 (2006.01)

(52) U.S. Cl. ..................................... 351/177; 351/159
(58) Field of Classification Search ................ 351/177, 351/159, 41, 168, 169, 170–172
See application file for complete search history.

(56) References Cited

U.S. PATENT DOCUMENTS

| 6,827,442 B1* | 12/2004 | Ross et al. ................... 351/205 |
| 6,840,619 B1* | 1/2005 | Dreher ........................ 351/159 |
| 2005/0041206 A1* | 2/2005 | Vogelsang et al. .......... 351/200 |

FOREIGN PATENT DOCUMENTS

| EP | 1 154 302 A1 | 11/2001 |
| EP | 1 262 815 A2 | 12/2002 |
| JP | A 5-176894 | 7/1993 |
| JP | A 2000-66148 | 3/2000 |
| WO | WO 00/52517 | 9/2000 |

* cited by examiner

Primary Examiner—Jordan M. Schwartz
(74) Attorney, Agent, or Firm—Oliff & Berridge, PLC

(57) ABSTRACT

A spectacle lens optical value determining method, a spectacle lens manufacturing method, a spectacle lens, and an order placing/receiving system of the same, which enable minimization of "sway" and "distortion" that one feels when wearing spectacles, are provided. An optical value of a spectacle lens is selected and determined so that a wavefront entering an eye of a subject at the time of optometry and a wavefront entering the eye when the subject wears the spectacle lens and views an object coincide with or are approximate to each other.

19 Claims, 21 Drawing Sheets

DIRECTION OF NEAR VISUAL LINE

Fig.5

ASTIGMATISM DISTRIBUTION     AVERAGE DIOPTER DISTRIBUTION

Fig. 8

ASTIGMATISM DISTRIBUTION    AVERAGE DIOPTER DISTRIBUTION

Fig.11

ASTIGMATISM DISTRIBUTION  AVERAGE DIOPTER DISTRIBUTION

Fig.14

TABLE 1

| DIAMETER | POWER | CONVEX SURFACE R(mm) | CENTER THICKNESS(mm) | REFRACTIVE INDEX |
|---|---|---|---|---|
| 36 | − 0.120 | 105.100 | 1.8 | ne=1.525 |
| 36 | − 0.25 | 105.100 | 1.8 | |
| 36 | − 0.37 | 105.100 | 1.7 | |
| 36 | − 0.50 | 105.100 | 1.7 | |
| 36 | − 0.62 | 105.100 | 1.7 | |
| 36 | − 0.75 | 105.100 | 1.7 | |
| 36 | − 0.87 | 105.100 | 1.7 | |
| 36 | − 1.00 | 105.100 | 1.6 | |
| 36 | − 1.25 | 105.100 | 1.6 | |
| 36 | − 1.50 | 105.100 | 1.6 | |
| 36 | − 1.75 | 105.100 | 1.6 | |
| 36 | − 2.00 | 105.100 | 1.6 | |
| 36 | − 2.25 | 131.110 | 1.3 | |
| 36 | − 2.50 | 131.110 | 1.3 | |
| 36 | − 2.75 | 131.110 | 1.3 | |
| 36 | − 3.00 | 131.110 | 1.3 | |
| 36 | − 3.25 | 131.110 | 1.3 | |
| 36 | − 3.50 | 131.110 | 1.3 | |
| 36 | − 3.75 | 131.110 | 1.3 | |
| 36 | − 4.00 | 131.110 | 1.3 | |
| 36 | − 4.25 | 174.590 | 1.3 | |
| 36 | − 4.50 | 174.590 | 1.3 | |
| 36 | − 4.75 | 174.590 | 1.3 | |
| 36 | − 5.00 | 174.590 | 1.3 | |
| 36 | − 5.25 | 174.590 | 1.0 | |
| 36 | − 5.50 | 174.590 | 1.0 | |
| 36 | − 5.75 | 174.590 | 1.0 | |
| 36 | − 6.00 | 174.590 | 1.0 | |
| 36 | − 6.25 | 262.000 | 1.0 | |
| 36 | − 6.50 | 262.000 | 1.0 | |
| 36 | − 7.00 | 262.000 | 1.0 | |
| 36 | − 8.00 | 262.000 | 1.0 | |
| 36 | − 9.00 | 262.000 | 1.0 | |
| 36 | − 10.00 | 262.000 | 1.0 | ▼ |
| 36 | + 0.12 | 105.100 | 2.1 | ne=1.525 |
| 36 | + 0.25 | 105.100 | 2.1 | |
| 36 | + 0.37 | 105.100 | 2.1 | |
| 36 | + 0.50 | 105.100 | 2.1 | |
| 36 | + 0.62 | 105.100 | 2.0 | |
| 36 | + 0.75 | 105.100 | 2.0 | |
| 36 | + 0.87 | 105.100 | 2.0 | |
| 36 | + 1.00 | 105.100 | 2.0 | |
| 36 | + 1.25 | 95.720 | 2.2 | |
| 36 | + 1.50 | 95.720 | 2.2 | |
| 36 | + 1.75 | 95.720 | 2.2 | |
| 36 | + 2.00 | 95.720 | 2.3 | |
| 36 | + 2.25 | 88.400 | 2.6 | |
| 36 | + 2.50 | 88.400 | 2.7 | |
| 36 | + 2.75 | 88.400 | 2.7 | |
| 36 | + 3.00 | 88.400 | 2.7 | |
| 36 | + 3.25 | 73.740 | 3.1 | |
| 36 | + 3.50 | 73.740 | 3.1 | |
| 36 | + 3.75 | 73.740 | 3.4 | |
| 36 | + 4.00 | 73.740 | 3.4 | |
| 36 | + 4.25 | 65.080 | 3.6 | |
| 36 | + 4.50 | 65.080 | 3.6 | |
| 36 | + 4.75 | 65.080 | 3.8 | |
| 36 | + 5.00 | 65.080 | 3.8 | |
| 36 | + 5.25 | 58.550 | 3.9 | |
| 36 | + 5.50 | 58.550 | 3.9 | |
| 36 | + 5.75 | 58.550 | 3.9 | |
| 36 | + 6.00 | 58.550 | 4.0 | |
| 36 | + 6.25 | 53.000 | 4.0 | |
| 36 | + 6.50 | 53.000 | 4.1 | |
| 36 | + 7.00 | 53.000 | 4.2 | |
| 36 | + 8.00 | 48.750 | 4.2 | |
| 36 | + 9.00 | 45.270 | 4.8 | |
| 36 | + 10.00 | 42.300 | 4.8 | ▼ |

Fig.17

EMBODIMENT 1

| WAVEFRONT ON REAR VERTEX SPHERE SURFACE | | S | C | Ax | AVERAGE DIOPTER |
|---|---|---|---|---|---|
| DISTANCE VISION (INFINITE FAR POINT) | TARGET VALUE | +4.00 | 0 | 90 | +4.00 |
| | DESIGN RESULT (y=+8mm,z=0mm ON LENS) | +4.14 | −0.29 | 90 | +4.00 |
| NEAR VISION (350mm FROM CORNEAL VERTEX) | TARGET VALUE | +3.48 | −0.04 | 90 | +3.46 |
| | DESIGN RESULT (y=−14.0mm and z=+2.7mm ON LENS) | +3.91 | −0.90 | 104 | +3.46 |

Fig.18

EMBODIMENT 2

| WAVEFRONT ON REAR VERTEX SPHERE SURFACE | | S | C | Ax | AVERAGE DIOPTER |
|---|---|---|---|---|---|
| DISTANCE VISION (INFINITE FAR POINT) | TARGET VALUE | −5.00 | 0 | 90 | −5.00 |
| | DESIGN RESULT (y=+8mm,z=0mm ON LENS) | −4.85 | −0.30 | 90 | −5.00 |
| NEAR VISION (350mm FROM CORNEAL VERTEX) | TARGET VALUE | −5.41 | −0.02 | 90 | −5.42 |
| | DESIGN RESULT (y=−14.0mm and z=+2.1mm ON LENS) | −5.38 | −0.10 | 104 | −5.43 |

Fig.19

EMBODIMENT 3

| WAVEFRONT ON REAR VERTEX SPHERE SURFACE | | S | C | Ax | AVERAGE DIOPTER |
|---|---|---|---|---|---|
| DISTANCE VISION (INFINITE FAR POINT) | TARGET VALUE | +4.00 | −2.03 | 90 | +2.99 |
| | DESIGN RESULT (y=+8mm,z=0mm ON LENS) | +4.05 | −2.10 | 90 | +3.00 |
| NEAR VISION (350mm FROM CORNEAL VERTEX) | TARGET VALUE | +3.50 | −2.01 | 90 | +2.50 |
| | DESIGN RESULT (y=−14.0mm and z=+2.1mm ON LENS) | +3.29 | −1.58 | 104 | +2.50 |

Fig.20

EMBODIMENT 4

| WAVEFRONT ON REAR VERTEX SPHERE SURFACE | | S | C | Ax | AVERAGE DIOPTER |
|---|---|---|---|---|---|
| DISTANCE VISION (INFINITE FAR POINT) | TARGET VALUE | +4.00 | 0 | 90 | +4.00 |
| | DESIGN RESULT (y=+8mm,z=0mm ON LENS) | +4.15 | −0.30 | 90 | +4.00 |
| NEAR VISION(1m FROM CORNEAL VERTEX AT TIME OF OPTOMETRY,350mm FROM CORNEAL VERTEX AT TIME OF DESIGN) | TARGET VALUE | +3.03 | −0.08 | 90 | +2.99 |
| | DESIGN RESULT (y=−14.0mm and z=+2.1mm ON LENS) | +3.41 | −0.83 | 104 | +3.00 |

METHOD FOR DETERMINING OPTICAL VALUE OF LENS OF EYEGLASSES, PROCESS FOR PRODUCING LENS OF EYEGLASSES, LENS OF EYEGLASSES AND ITS ORDERING/ORDR RECEIVING SYSTEM

TECHNICAL FIELD

The present invention relates to a spectacle lens optical value determining method capable of obtaining a spectacle lens more suitable for the patient, a spectacle lens manufacturing method, a spectacle lens, and an order placing/receiving system of the same.

BACKGROUND ART

For example, in a lens region of a progressive-addition lens, there are a region of a distance portion for distance vision, a portion for near vision, and a region of an intermediate vision for viewing objects at intermediate distances. A positive refractive power is progressively added from the region of the distance portion through the region of the intermediate vision to the region of the near portion. The difference in refractive power between the region of the distance portion and the region of the near portion of the progressive-addition lens is called an addition power. For a person wearing spectacles for presbyopia who has insufficient power of accommodation in near vision, the addition is designated in accordance with the degree of presbyopia so as to allow comfortable near vision by complementing the power of accommodation. Typically, the addition power of a progressive-addition lens is designated at a value in a range from 0.25 D to 4.00 D by increments of 0.25 D in accordance with the degree of presbyopia and/or the near working distance.

The order information must include an addition power if the order is placed by an optician for a progressive-addition lens with a spectacle lens manufacturer. As described above, the progressive-addition lens has the refractive power varying from the region of the distance portion through the region of the intermediate vision to the region of the near portion in accordance with the designated addition power. Therefore, when the progressive-addition lens is used as a spectacle lens, the size of an object to be viewed varies in respective visual regions of the lens, which causes a person wearing the spectacles to feel "sway" or "distortion". The "sway" and "distortion" of the progressive-addition lens tend to increase with an increase in the addition power. To make the "sway" and "distortion" small enough, various attempts have conventionally been proposed to decrease as much as possible the "sway" and "distortion" of lenses with the same addition power by devising the refractive power distribution of the progressive-addition lens (see, for example, Patent Document 1).

Patent Document 1: Japanese Unexamined Patent Publication No. 2000-66148

DISCLOSURE OF THE INVENTION

However, when the addition power provided to a progressive-addition lens is not enough with respect to the degree of presbyopia of a person wearing spectacles, his or her insufficient power of accommodation is not fully complemented. Thus, when the person wearing spectacles views a near object through the region of the near portion, he or she feels dissatisfaction at seeing the object out of focus and blurred due to insufficient power of accommodation when bringing the object closer to a necessary distance to view.

On the other hand, when the addition power provided to a progressive-addition lens is excessive for the degree of presbyopia of a person wearing spectacles, his or her insufficient power of accommodation is excessively complemented. Thus, when the person wearing spectacles views a near object through the region of the near portion, he or she cannot see the object unless by bringing it closer than necessary, and additionally often feels dissatisfaction at recognizing the abovementioned "sway" or "distortion". Therefore, it is very important to provide an adequate addition power to spectacles using progressive-addition lenses in accordance with the degree of presbyopia of a person wearing spectacles. Accordingly, it is extremely important to perform appropriate optometry when a spectacle lens is ordered, and spectacles are manufactured based on the adequate prescription values obtained from the optometry.

According to study by the present inventor, however, especially for the progressive-addition spectacle lens, it has been found that there are sometimes cases in which spectacles manufactured based on prescription values that are considered to be adequate obtained by performing appropriate optometry are not always small enough in the aforementioned "sway" and "distortion".

It is an object of the present invention to provide a spectacle lens optical value determining method, a spectacle lens manufacturing method, a spectacle lens, and an order placing/receiving system of the same, which enable minimization of "sway" and "distortion" that one feels when wearing spectacles.

The present invention as means which solves the above problems is made based on the following results of clarification. Specifically, it has been found in the study by the present inventor that one of the main reasons why the spectacles manufactured based on the prescription value considered to be adequate are not always small enough in "sway" and "distortion" is that optical conditions at the time of optometry and optical conditions at the time of actually wearing the spectacles manufactured based on the prescription value obtained from the optometry are not equivalent, and the unequivalence is at a non-negligible level. In addition, it has been also realized that there are many kinds of optometry methods, and the optical conditions are non-negligibly different according to the kinds.

More specifically, in the description with, for example, a progressive-addition lens as an example, there are following four known methods as optometry methods currently employed to determine the addition power and so on. FIG. 15 is an explanatory view of trial lens and an eyeglass test frame used in a subjective optometry method by a lens exchange method. The eyeglass test frame has mounting positions for mounting three to four trial lenses so that when a plurality of trial lenses are mounted, a low power trial lens is mounted on the outer side (object side) and a high power trial lens is mounted on the inner side (eye side). The following is the description of this subjective optometry method using the test frame and exchanging trial lenses.

To find the addition power to a progressive-addition lens necessary for a patient, a state of distance prescription for the patient to have comfortable distance vision, that is, to be able to view a character, for example, 5 m ahead is established first in advance through use of the trial lens and eyeglass test frame. Since the method until establishment of this distance prescription state is common in the following addition determining methods, the state is considered as being obtained by a general optometry method and is thus not described in detail here. The difference among the method for determining the addition power of a progressive-addition lens exists in the process after the establishment of the distance prescription state.

A first method for determining the addition power of a progressive-addition lens by actual optometry will be described below. In the distance prescription state in which a trial lens with a power adequate for distance vision is mounted on an eyeglass test frame, a power of a trial lens is selected which is a spherical power to enable a patient to have comfortable near vision, that is, to be able to view a character, for example, 40 cm ahead. This trial lens is additionally inserted into a trial lens mounting position on the outer side (object side) of the eyeglass test frame in the distance prescription state. The spherical power of the trial lens later added to the outer side of the eyeglass test frame is regarded as the addition power. Hereinafter, this first method is referred to as a "near vision lens addition mode".

A second method for determining the addition power to a progressive-addition lens will be described below. In the distance prescription state in which a trial lens with a power adequate for distance vision is mounted on an eyeglass test frame, a spherical power lens of the trial lens is exchanged with another to select a spherical power of the trial lens to enable a patient to have comfortable near vision, that is, to be able to view a character, for example, 40 cm ahead, thereby obtaining a prescription state for near vision. The difference in the spherical power between the trial lens with the spherical power in the near prescription state and the trial lens with the spherical power in the distance prescription state is regarded as the addition power. Hereinafter, this second method is referred to as a "distance vision/near vision lens power difference mode".

A third method for determining the addition power to a progressive-addition lens will be described below. There is a subjective optometry method by a lens exchange method using a refractor head, a method of finding the prescription power for distance vision and the prescription power for near vision so as to regard the difference in the spherical power between them as the addition power. However, since the near vision when using the refractor head of an optometry apparatus has a narrower visual field than that when using an eyeglass test frame, the near vision is performed in substantially the same direction as that of the distance visual line. Therefore it is preferable to classify this method as "distance vision/near vision lens power difference mode by a refractor head" because the direction of the near vision differs from that of the "distance vision/near vision lens power difference mode" using the eyeglass test frame.

A fourth method for determining the addition power to a progressive-addition lens will be described below. In the distance prescription state in which trial lenses with a power adequate for distance vision is mounted on an eyeglass test frame, the critical near distance, that is, the nearest distance that the patient can have clear vision (can clearly view) is measured so that its reciprocal is regarded as the power of accommodation to the patient. This arrangement is made from a concept of how much power of accommodation should be complemented by a spectacle lens in order to enable the patient to have comfortable clear vision at a near work distance that is desired by the patient. The difference between the reciprocal of the near work distance and the power of accommodation, i.e. the reciprocal of the critical near distance, of the patient is regarded as the addition power. In the fourth method, use of the refractor head of the optometry apparatus is also possible, but the distance visual line and the near visual line are in substantially the same direction as described in the third method. As for the method and apparatus, the following is proposed by the present applicant.

Patent Document 2: Japanese Unexamined Patent Publication No. Hei 5-176894

As described above, the configurations of the trial lens optical systems in the respective optometry methods are different. This is the reason why the wavefront entering a patient's eye when he or she views a near object, the wavefront being made at the time of optometry, is slightly different among the optometry methods. Besides, it is typical that the optical system at the time of optometry and the optical system at the time of actually wearing spectacles using a manufactured lens do not coincide with each other as described above, and these optical conditions are also different, which also makes the wavefronts different. Unless the wavefront entering an eye at the time of wearing spectacles coincides with the wavefront entering the eye at the time of optometry, it is impossible to obtain the same optical performance obtained at the time of optometry.

The present invention is made based on the above results of clarification, and is characterized in that an optical value of a spectacle lens is selected and determined so that a wavefront entering an eye of a subject at the time of optometry and a wavefront entering the eye when the subject wears the spectacle lens and views an object coincide with or are approximate to each other.

Specifically, for example, the wavefront entering an eye when a patient in a state of wearing a progressive-addition lens to be produced views a near object is calculated to determine the addition power to the progressive-addition lens so that the wavefront becomes the same as the wavefront entering the eye of the patient at the time of optometry. In this case, the distance refractive power is determined by the wavefront shape on the rear vertex sphere when a pencil of ray from infinite far away (plane wavefront) is incident, in the trial lens optical system when the distance vision power has been determined. The near refractive power is determined by the wavefront shape on the rear vertex sphere when a pencil of ray from a near object point (spherical wavefront) is incident, in the trial lens optical system when the near vision power has been determined. This means that it is sufficient that the wavefronts the same as those at the time of optometry are created in both the distance vision and the near vision at the time of wearing the progressive-addition lens.

To calculate the wavefront at the time of optometry, information of the trial lens optical system at the time of optometry is required. When an optician places an order for a progressive-addition lens with a spectacle lens manufacturer, the optician has conventionally designated only the value of the addition power but has not provided, in order information of a lens, identification information of the addition power determining method, that is, what method has been used to determine the addition power at the time of optometry. As a result, even if an appropriate addition power is determined by optometry, the identification information of the addition power determining method at the time of optometry is not included in the order information of a lens, and therefore sufficient information to provide the appropriate addition power to an actual progressive-addition lens has not been passed to the spectacle lens manufacturer.

The present invention provides identification information of the addition power determining method, that is, what method has been used to determine the addition power at the time of optometry, to order information of a progressive-addition lens which is passed from an optician side to a spectacle lens manufacturer, so that a practical refractive power provided to a lens when the progressive-addition lens is manufactured can have an appropriate value which is nether too much nor too little.

Further, the present invention is also applicable to a progressive-addition semi-finished lens blank (hereinafter referred to as a progressive-addition semi-lens) whose first surface (a surface on the object side) being a progressive surface has been finished in advance. A progressive-addition lens whose first surface (a surface on the object side) is a progressive surface is manufactured by processing the progressive-addition semi-lens. The progressive surface being the first surface of this progressive-addition semi-lens has been often made in advance in mass production in which the amount of increase in surface refractive power within a region of a near vision with reference to the surface refractive power within a region of a distance vision is used as the addition power of the progressive surface.

The addition power of the progressive surface of the progressive-addition semi-lens is set within a range, for example, from 0.75 D to 3.50 D by increments of 0.25 D for mass production. For such a progressive-addition semi-lens whose first surface is a progressive surface, the shape of the progressive surface cannot be designed in such a manner to reproduce the wavefront of a transmitted light at the time of optometry as described above to every prescription order because the progressive surface has been finished in advance. In this case, a better progressive-addition lens can be manufactured by selecting, from among the progressive-addition semi-lenses, a lens with the addition power of a progressive surface with which a wavefront the closest to the wavefront of the transmitted light at the time of optometry can be obtained when the lens is finished as a progressive-addition lens, and processing its second surface.

BRIEF DESCRIPTION OF DRAWINGS

FIG. 1 is an optical path diagram at the time of optometry of a spectacle lens according to an embodiment 1, in which

FIG. 5 is an interface screen for finding a wavefront entering an eye by performing ray tracing with a computer;

FIG. 7 is an optical path diagram at the time of optometry of a spectacle lens according to an embodiment 3, in which

FIG. 8 is an interface screen for finding a wavefront entering an eye by performing ray tracing with a computer;

FIG. 11 is an interface screen for finding a wavefront entering an eye by performing ray tracing with a computer;

FIG. 14 is a mathematical table showing shapes of standard trial lenses;

FIG. 17 is an input/output data table of the embodiment 1;

FIG. 18 is an input/output data table of the embodiment 2;

FIG. 19 is an input/output data table of the embodiment 3;

FIG. 20 is an input/output data table of the embodiment 4;

Figure 1A:
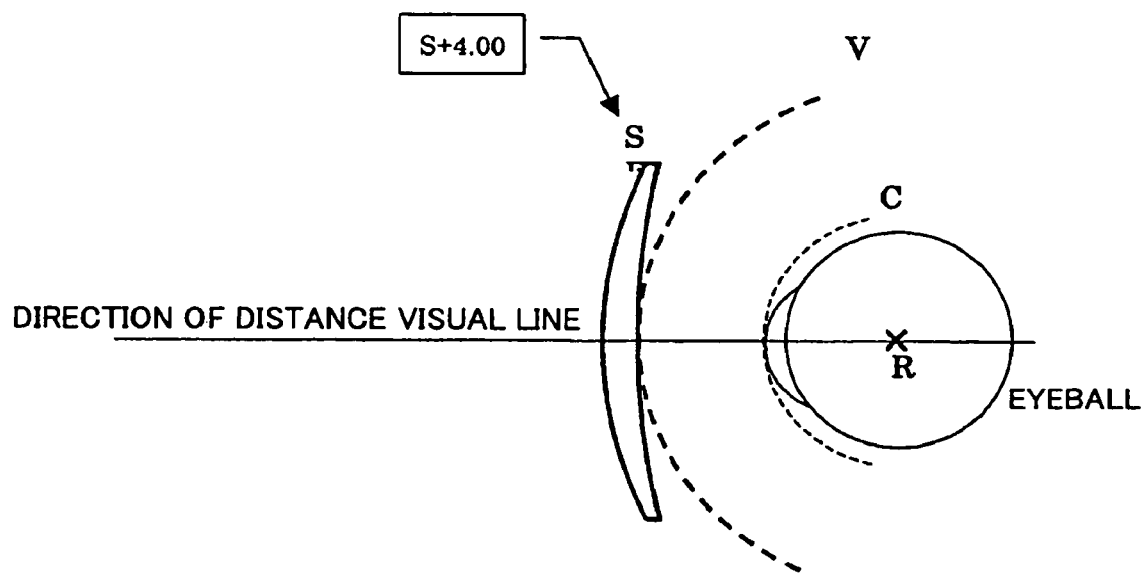
FIG. 1(a) is a diagram of an optical path in a direction of a distance visual line.

V0 rear vertex sphere
C corneal vertex sphere
R center of rotation of an eye
1 distance vision power test lens layout
2 distance vision lens layout power input section
3 distance vision lens surface information input section
4 distance vision lens VC/CR input section
5 distance vision lens principal ray passing point input section
6 far ray tracing start switch section
7 far ray tracing result output section
8 near vision power test lens layout
9 near vision lens layout power input section
10 near vision lens surface information input section
11 near vision lens VC/CR input section
12 near vision lens principal ray passing point input section
13 near ray tracing start switch section
14 near ray tracing result output section
100 optician
101 terminal unit
102 frame shape measuring instrument
200 factory (spectacle lens manufacturer)
201 mainframe (processing unit)
202 LAN
210 terminal unit
211 rough edging apparatus (curve generator)
212 sanding polisher
220 terminal unit
221 lens meter
222 wall thickness meter
230 terminal unit
231 marker
232 image processor
240 terminal unit 241 lens cutting machine
242 chuck interlock
250 terminal unit
251 shape measuring instrument
300 public communication line

BEST MODE FOR CARRYING OUT THE
INVENTION

Embodiment 1

Figure 1B:
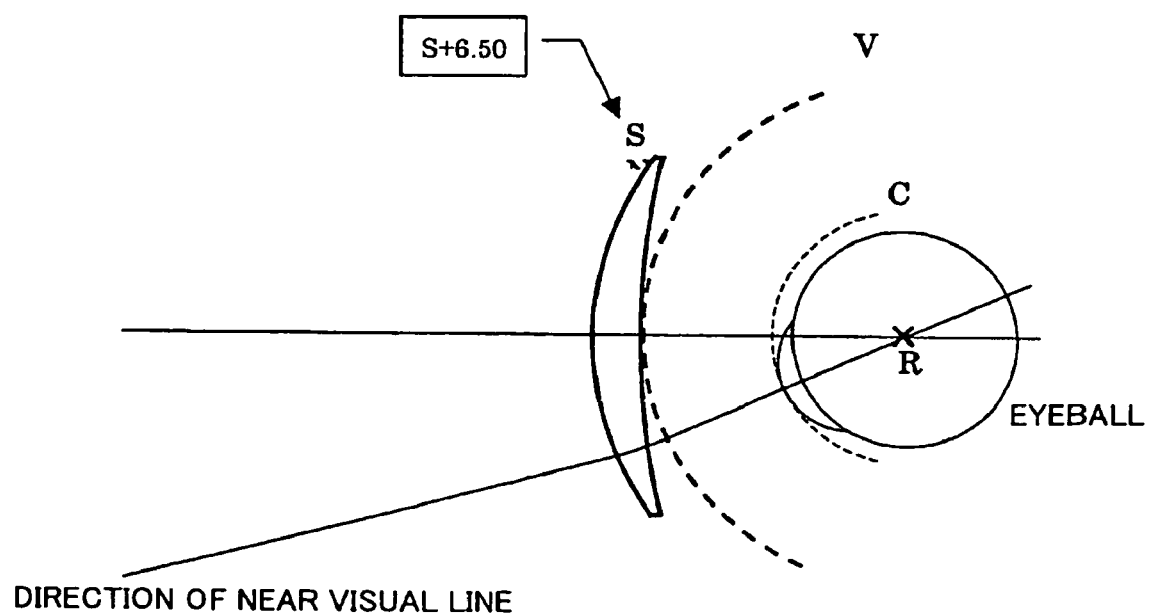
FIG. 1(b) is a diagram of an optical path in a direction of a near visual line.
Figure 2:
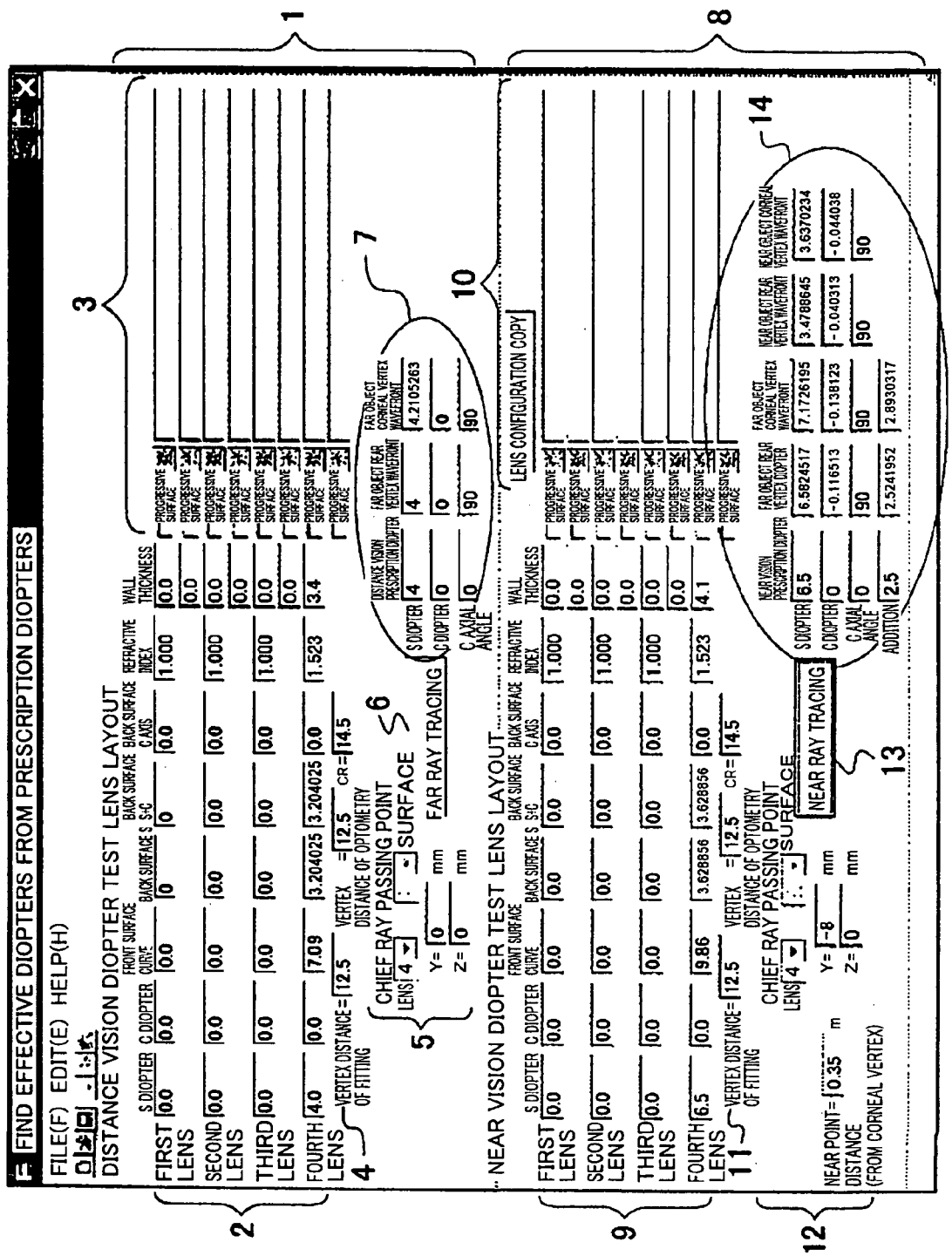
FIG. 2 is an interface screen for finding a wavefront entering an eye by performing ray tracing with a computer.
Figure 3:
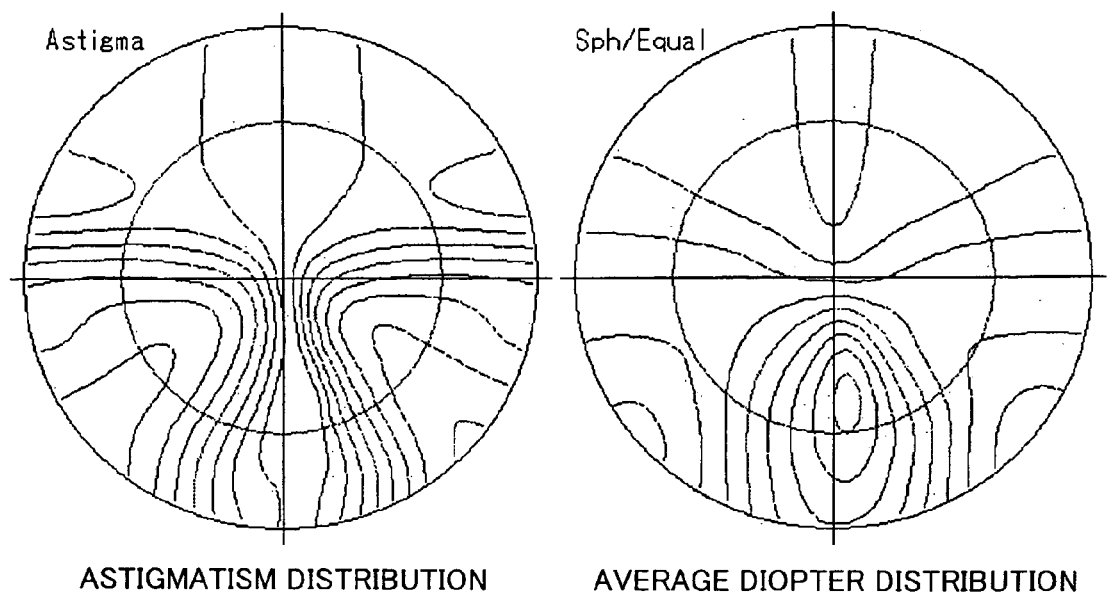
FIG. 3 is an astigmatism distribution diagram and a diagram showing an average power of a spectacle lens with determined optical values.

FIG. 1 is an optical path diagram at the time of optometry of a spectacle lens according to an embodiment 1, in which FIG. 1(*a*) is a diagram of an optical path in a direction of a distance visual line, and FIG. 1(*b*) is a diagram of an optical path in a direction of a near visual line, FIG. 2 is an interface screen for finding a wavefront entering an eye by performing ray tracing with a computer, FIG. 3 is a diagram showing an astigmatism distribution and an average power of a spectacle lens with determined optical values, and FIG. 17 is a table in which input and output data are summarized. Referring to these drawings, a spectacle lens optical value determining method, a spectacle lens manufacturing method, a spectacle lens, and an order placing/receiving system thereof, which are according to the embodiment 1, will be described below. It should be noted that this embodiment is an example of a spectacle lens that is a progressive-addition lens and is the above-described "distance vision/near vision lens power difference mode", corresponding to the second method for determining the addition power of a progressive-addition lens.

The spectacle lens optical value determining method according to this embodiment finds a wavefront at the time of optometry, applies a ray tracing method, with the wavefront regarded as a target wavefront, to an optical system in a state in which a wearer wears spectacles using a spectacle lens to be manufactured, and determines the refractive power and so on of a lens so that the wavefront becomes the above-described target wavefront.

To find the wavefront at the time of optometry or wearing the spectacles, a computer is used which calculates the wavefront by the ray tracing method. This computer is designed such that curve values representing shapes of a front surface and a rear surface of each lens, a refractive index of material, a central thickness, a distance between lenses, a distance from a rear vertex to a corneal vertex, a distance from the corneal vertex to a center of rotation, a position of a passing point of a principal ray, a ray that is emitted from an object point, passes through a lens, and then directs to the center of rotation, can be inputted into an input/output screen (interface screen) of the computer to obtain calculation results on the wavefront displayed thereon. It should be noted that this program is capable of coping also with a case in which the lens surface is a specific surface (for example, a progressive surface).

Figure 15:
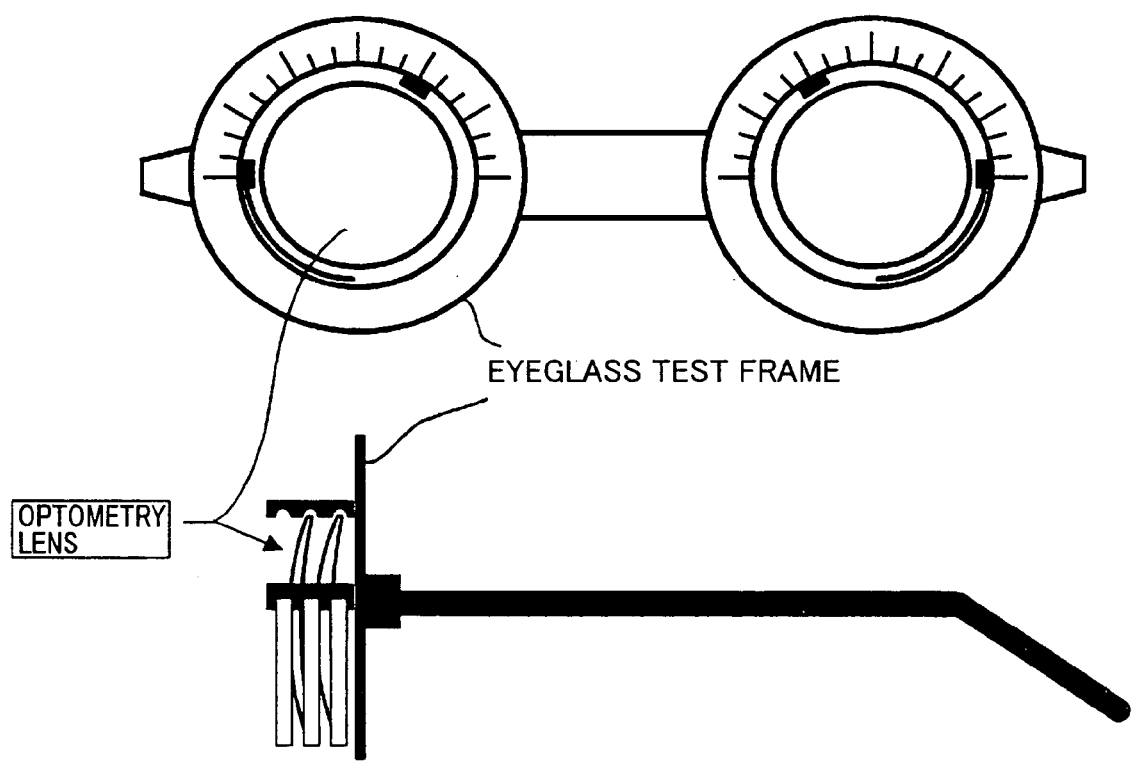
FIG. 15 is an explanatory view of a trial lens and an eyeglass test frame used in a subjective optometry method by a lens exchange method.

In this case, the optometry should be performed by a subjective optometry method by a lens exchange method using a trial lens and an eyeglass test frame as shown in FIG. 15. The eyeglass test frame is designed such that four, first to fourth, trial lenses can be mounted in a freely exchangeable manner. It should be noted that the trial lenses are named first, second, third, and fourth lenses in order from farthest to closest to an eye.

A calculating method of a wavefront will be described below. The wavefront is a surface with a fixed optical path length from a light source. A wavefront at one point on a ray is orthogonal to the ray. A wavefront emitted from a point light source is a sphere, and its radius is a radius from the point light source. In other words, the wavefront changes in shape when propagated. The shape of the wavefront also changes by being refracted by a lens. The calculation of the wavefront means calculation of a change in the wavefront due to propagation in a uniform medium and a change due to refraction on an interface between different media.

First, a tracing method of a change in the wavefront due to refraction will be described. As in FIG. 21, an incident ray is refracted at P point on a boundary surface. The refractive index of a medium on an incident side is defined as N and the refractive index on an exit side as N', the incident angle as θ, and the exit angle as θ'. According to Snell's laws, a normal to the boundary surface and the incident and exit rays at P point exist within the same plane and N sin θ=N' sin θ'.

Figure 21:
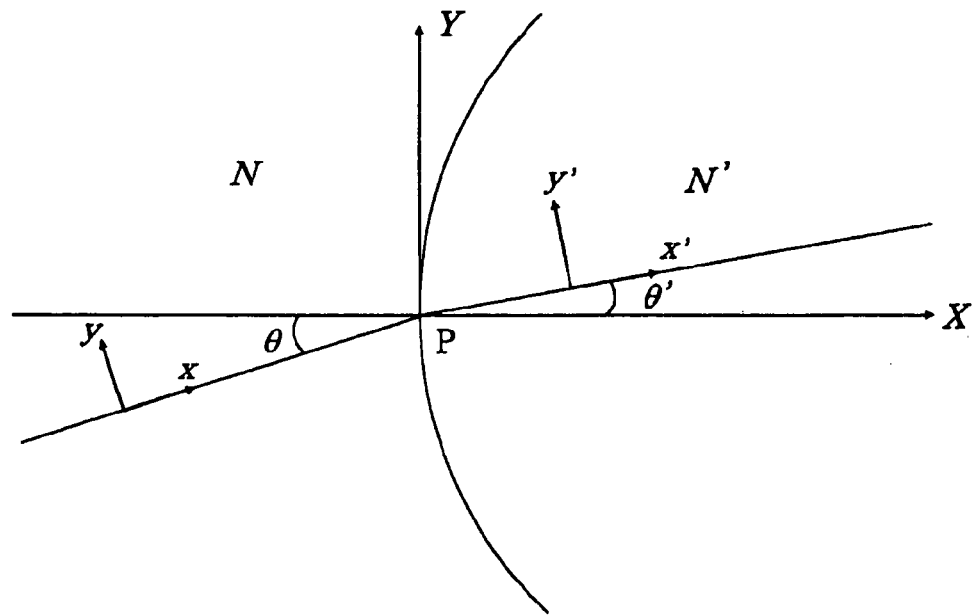
FIG. 21 is a coordinate system showing a wavefront on a refraction surface.

This plane is called a ray plane. FIG. 21 shows coordinate axes for presenting the wavefront. A local coordinate system x-y-z representing the incident wavefront has a point of origin at P, but is illustrated with the x-y axes slightly shifted for easy understanding. The x axis is in a direction along the incident ray, and the y axis is orthogonal to the x axis. Both the axes exist within the ray plane. The z axis, which is determined in accordance with the corkscrew rule, is vertical to the ray plane. A local coordinate system x'-y'-z' representing the exit wavefront is also determined in a similar manner. A local coordinate system X-Y-Z representing the shape of the boundary surface near P point is also determined in a similar manner. The above three local coordinate systems have x axes and y axes existing within the ray plane and the same z axis.

The incident wavefront can be expressed by the following equation, with omission of terms of third degree or higher.

$$x = \frac{1}{2}C_y y^2 + \frac{1}{2}C_z z^2 + C_{yz} yz \qquad \text{(Equation 1)}$$

Here, $C_y$, $C_z$, $C_{yz}$ are parameters of the incident wavefront. For a spherical wavefront, $$C_y = C_z = \frac{1}{R},$$

$C_{yz}=0$, and R is a radius. When $C_y \neq C_z$ or $C_{yz} \neq 0$, the wavefront is a cylindrical wavefront. The cylindrical power is calculated by $C=\sqrt{(C_y-C_z)^2+4C_{yz}^2}$, and the axial angle α is calculated by $$\tan 2\alpha = \frac{2C_{yz}}{C_y - C_z}.$$

Similarly, the exit wavefront can be expressed by the following equation, with omission of terms of third degree or higher.

$$x' = \frac{1}{2}C_{y'} y'^2 + \frac{1}{2}C_{z'} z'^2 + C_{y'z'} y'z' \qquad \text{(Equation 2)}$$

Here, $C_{y'}$, $C_{z'}$, $C_{y'z'}$ are parameters of the exit wavefront.

Similarly, the shape of the boundary surface near P point can be expressed by the following equation, with omission of terms of third degree or higher.

$$X = \frac{1}{2}C_Y Y^2 + \frac{1}{2}C_Z Z^2 + C_{YZ} YZ \quad \text{(Equation 3)}$$

Here, $C_Y$, $C_Z$, $C_{YZ}$ can be calculated by the shape of the boundary surface. Finding the change in the wavefront due to refraction means finding the exit wavefront parameters $C_{y'}$, $C_{z'}$, $C_{y'z'}$ from the already known incident wavefront parameters $C_y$, $C_z$, $C_{yz}$ and boundary surface parameters $C_Y$, $C_Z$, $C_{YZ}$.

Application of Snell's laws to rays at and near P point provides the following refraction equations.

$$C_{y'}\cos^2\theta' = \left|\frac{N}{N'}\right| C_y \cos^2\theta + GC_Y \quad \text{(Equation 4)}$$

$$C_{y'z'}\cos\theta' = \left|\frac{N}{N'}\right| C_{yz}\cos\theta + GC_{YZ}$$

$$C_{z'} = \left|\frac{N}{N'}\right| C_z + GC_Z$$

Here, $$G = \cos\theta' - \left|\frac{N}{N'}\right|\cos\theta.$$

In the foregoing, the tracing of the change in the wavefront due to refraction is described.

Figure 22:
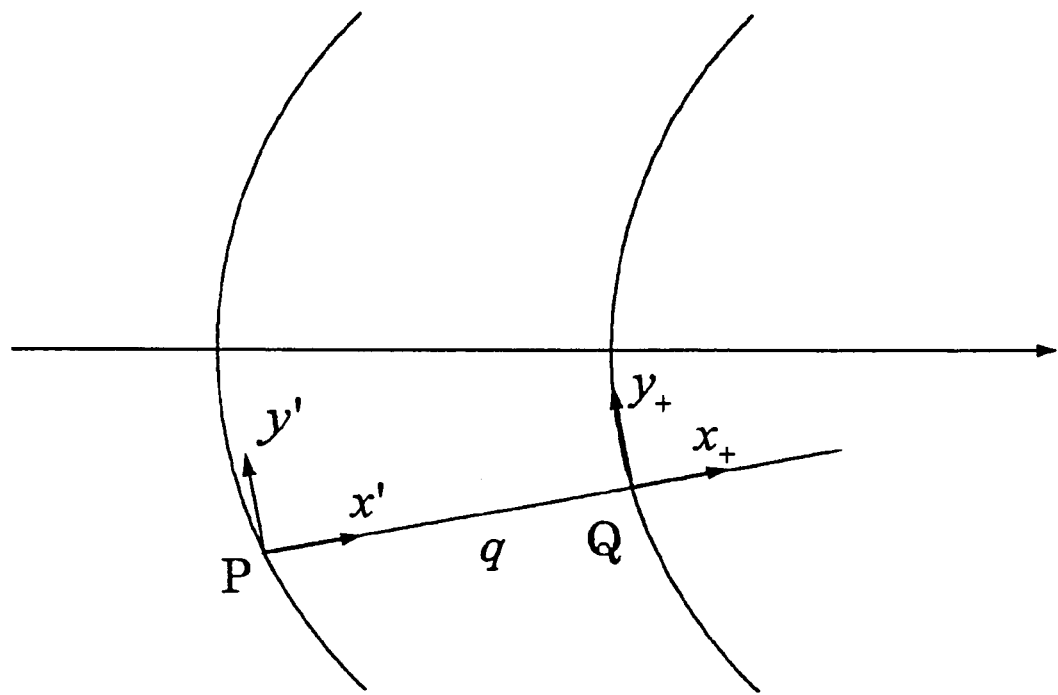
FIG. 22 is a coordinate system showing a wavefront by propagation in the same medium.

Next, tracing of a change in the wavefront due to propagation in the same medium will be described. As in FIG. 22, it is assumed that a ray exiting from P point intersects a subsequent boundary surface at Q point that is apart from P point by a distance q. The incident wavefront at Q point is a wavefront after the exit wavefront ($C_{y'}$, $C_{z'}$, $C_{y'z'}$) at P point is propagated by the distance q. Parameters $C_{y^\wedge}$, $C_{z^\wedge}$, $C_{y^\wedge z^\wedge}$ of the wavefront can be obtained from the following equations.

$$C_{y^\wedge} = \frac{C_{y'} + (C_{y'z'}^2 - C_{y'}C_{z'})q}{(1 - C_{y'}q)(1 - C_{z'}q) - C_{y'z'}^2 q^2} \quad \text{(Equation 5)}$$

$$C_{y^\wedge z^\wedge} = \frac{C_{y'z'}}{(1 - C_{y'}q)(1 - C_{z'}q) - C_{y'z'}^2 q^2}$$

$$C_{z^\wedge} = \frac{C_{z'} + (C_{y'z'}^2 - C_{y'}C_{z'})q}{(1 - C_{y'}q)(1 - C_{z'}q) - C_{y'z'}^2 q^2}$$

Figure 23:
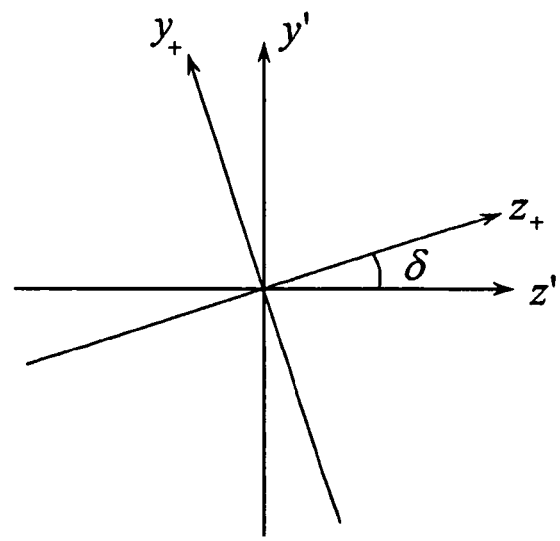
FIG. 23 is a diagram showing a difference in angle at a local coordinate between an incident ray and an exit ray.

Thus, the incident wavefront parameters at Q point are obtained, but the parameters cannot be substituted, as they are, into the equation for finding the exit wavefront at Q point. This is because generally the ray plane at Q point does not coincide with the ray plane at P point. Accordingly, a $y_+$ axis and a $z_+$ axis of the local coordinate of the incident ray at Q point do not sometimes coincide with the y' axis and z' axis of the local coordinate of the exit ray at P. As in FIG. 23, supposed that the angle between the $y_+$ axis and the y' axis is σ, $$y' = y_+ \cos\delta + z_+ \sin\delta$$

$$z' = -y_+ \sin\delta + z_+ \cos\delta$$

These are substituted into $$x = \frac{1}{2}C_{y^\wedge} y'^2 + \frac{1}{2}C_{z^\wedge} z'^2 + C_{y^\wedge z^\wedge} y'z',$$

and rearranged, leading to $$x = \frac{1}{2}C_{y+} y_+^2 + \frac{1}{2}C_{z+} z_+^2 + C_{y+z+} y_+ z_+,$$

so that $C_{y+}$, $C_{z+}$, $C_{y+z+}$ can be obtained from the following equations.

$$C_{y+} = \frac{1}{2}(C_{y^\wedge} + C_{z^\wedge}) + \frac{1}{2}(C_{y^\wedge} - C_{z^\wedge})\cos 2\delta - \quad \text{(Equation 6)}$$
$$C_{y^\wedge z^\wedge} \sin 2\delta$$

$$C_{z+} = \frac{1}{2}(C_{y^\wedge} + C_{z^\wedge}) - \frac{1}{2}(C_{y^\wedge} - C_{z^\wedge})\cos 2\delta +$$
$$C_{y^\wedge z^\wedge} \sin 2\delta$$

$$C_{y+z+} = \frac{1}{2}(C_{y^\wedge} - C_{z^\wedge})\sin 2\delta + C_{y^\wedge z^\wedge} \cos 2\delta$$

$C_{y+}$, $C_{z+}$, $C_{y+z+}$ are allowed to be substituted into the equation for finding the exit wavefront at Q point.

Even in the case in which there are a plurality of refractive boundary surfaces as in a lens, it becomes possible to find a final exit wavefront by repeating the above-described tracing of a change in the wavefront due to refraction and tracing of a change in the wavefront due to propagation. From $C_{y+}$, $C_{z+}$, $C_{y+z+}$ that are the parameters of this exit wavefront, the refractive power of a lens is calculated by the above-described method.

The foregoing describes the method for finding the exit wavefront from the incident wavefront to thereby calculate the refractive power of a lens.

Next, a geometrical optical calculating method of the refractive power of a lens will be described. The refractive power of a lens can be calculated from the refractive index of material, the radius of curvature of a lens surface, and the wall thickness. Besides, the curve value is a value obtained by dividing a constant by the radius of curvature of the lens surface and thus in an inversely proportional relationship therewith. The relationship between each parameter and the refractive power of a single lens can be expressed by the following general equation. Note that the following equation is an example of a case in which the lens surface is a sphere, but is usable even for a special surface (for example, a progressive surface) as long as it is limited to an arbitrary very small range.

$$D=\{(n-1)\cdot(1/R_1-1/R_2)+(n-1)^2/n\cdot t/(R_1\cdot R_2)\}\cdot K$$

$$K=\{1-t/n\cdot(n-1)/R_1\}^{-1}$$

$$C_1=523/R_1$$

$$C_2=523/R_2 \quad \text{(Equation 7)}$$

Note that,

D: refractive power n: refractive index of material t: wall thickness $C_1$: curve value of front surface $R_1$: radius of curvature of front surface $C_2$: curve value of rear surface $R_2$: radius of curvature of rear surface Software for numerically calculating the above-described mathematical equation is programmed and installed into a processing unit to create an input/output screen (interface screen) shown in FIG. 2. The input/output screen shown in FIG. 2 will be described below. A distance vision power test lens layout 1 is arranged at an upper portion of the screen, and a near vision power test lens layout 8 at a lower portion of the screen. The S power, C power, front surface curve, rear surface S, rear surface S+C, rear surface C axis, refractive index, and wall thickness interval or lens interval of a trial lens are inputted into a distance vision lens layout power input section 2. The lens surface information such as a progressive surface is inputted into a distance vision lens surface information input section 3. Respective rows for a first to a fourth lens correspond to positions into which trial lenses are inserted of the eyeglass test frame shown in FIG. 15. Into a distance vision lens VC/CR input section 4, the VC at the time of optometry, VC at the time of wearing, and CR are inputted. The VC at the time of optometry is a distance from a rear vertex to a corneal vertex of the fourth lens at the time of optometry. The VC at the time of wearing is a distance from a rear vertex to a corneal vertex of a spectacle lens. The arrangement is designed to allow separate input of the VC at the time of optometry and VC at the time of wearing. This is to put into consideration the difference in situation between the time of optometry and the time of wearing. The CR is a distance from the corneal vertex to a center of rotation.

The principal ray is a ray that is emitted from an object point, passes through a trial lens, and then directs to the center of rotation at the time of optometry. A position of a passing point of the principal ray can be designated at a distance vision lens principal ray passing point input section 5. After data input of the above conditions, a mouse click on a far ray tracing start switch section 6 causes execution of the above-described calculation. As a result of the calculation, the S power, C power, and C axial angle for each of the distance vision prescription power, far object rear vertex wavefront, and far object corneal vertex wavefront, are displayed in a far ray tracing result output section at 7.

In the near vision power test lens layout section 8, there are input boxes 9, 10 and 11 that are similar to those in the distance vision power test lens layout section 1. In a near vision lens principal ray passing point input section 12, an input box for a near working distance from a corneal vertex to an object point is added. After data input of the above conditions, a mouse click on a near ray tracing start switch section 13 causes execution of the above-described calculation. As a result of the calculation, the S power, C power, C axial angle, and addition power for each of the near vision prescription power, far object rear vertex power, far object corneal vertex wavefront, near object rear vertex wavefront, and near object corneal vertex wavefront, are displayed in a near ray tracing result output section 14.

Figure 5:
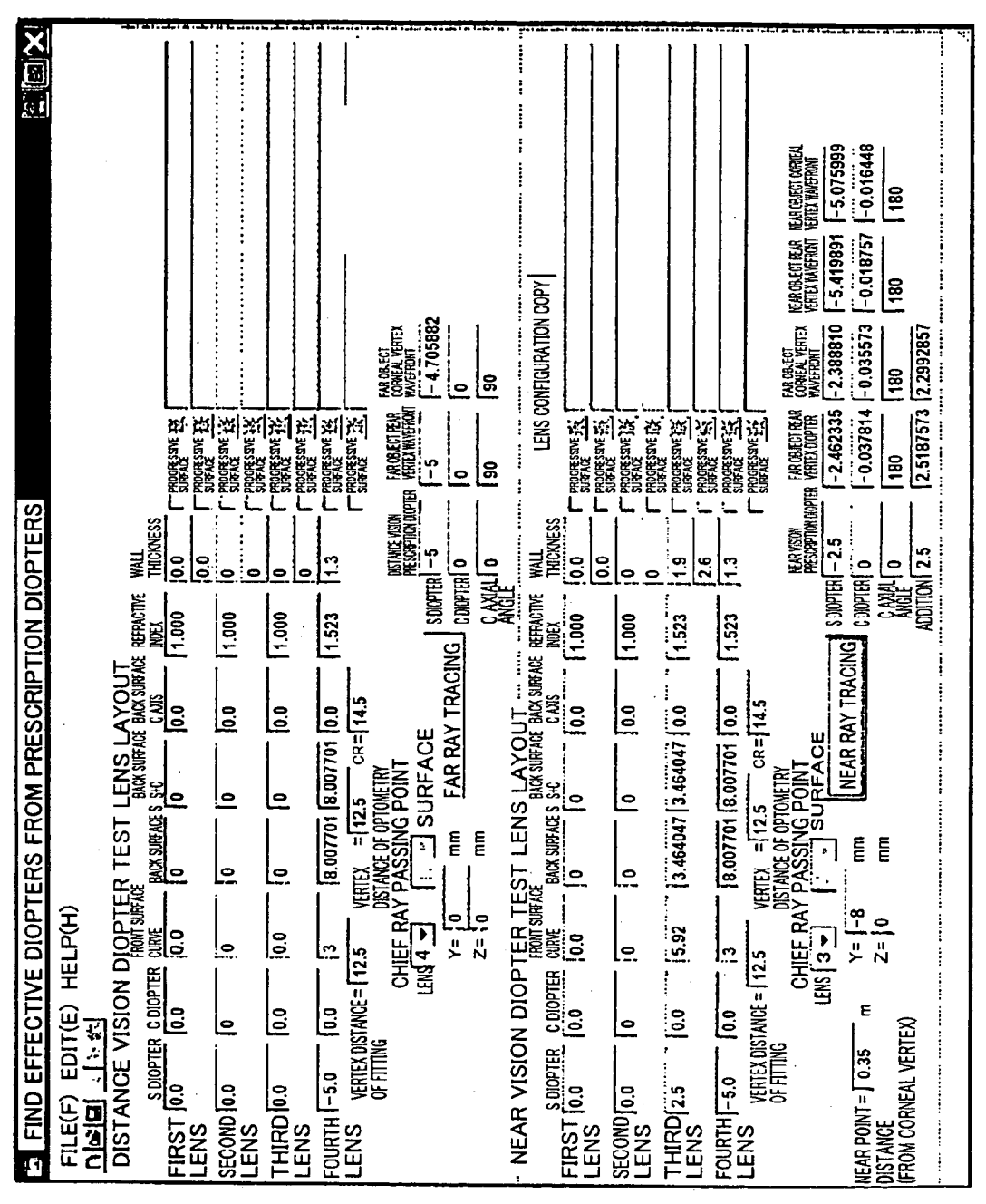
Figure 8:
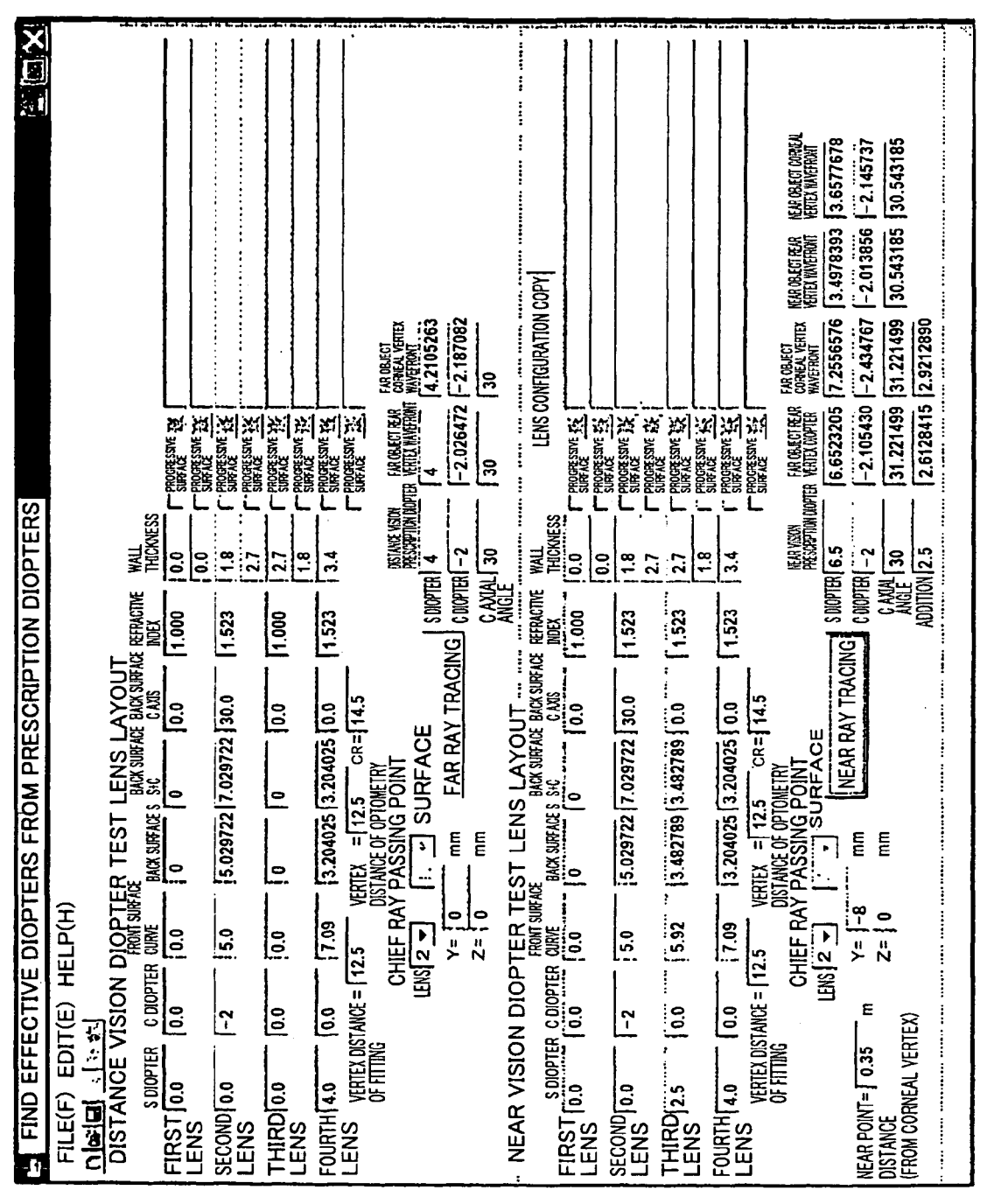
Figure 11:
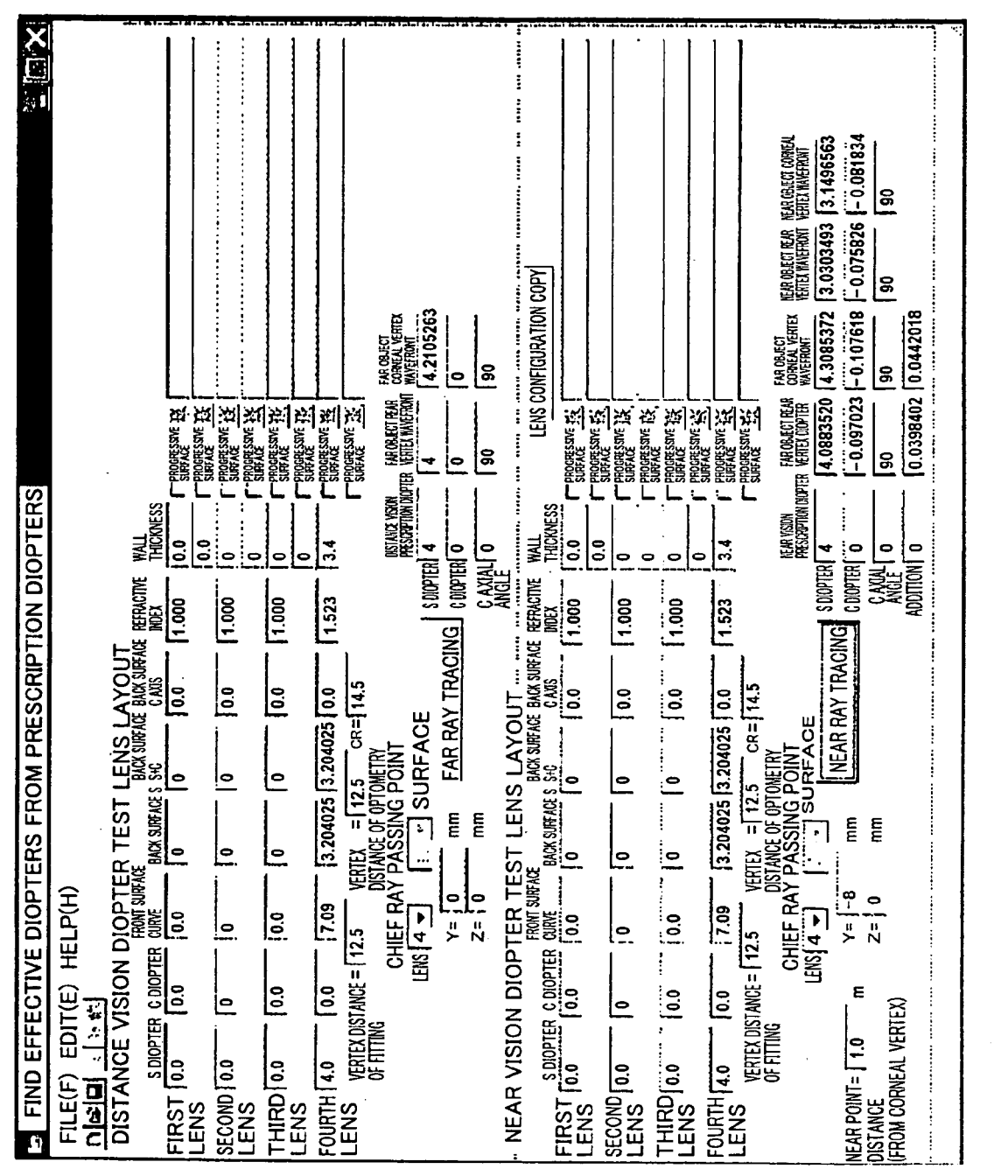

The screen layout described with FIG. 2 in the foregoing is in common with screen layouts of FIG. 5, FIG. 8 and FIG. 11 of the following embodiments.

In the example shown in FIG. 2, the distance refraction optometry value is S at +4.00 D, and there is only one trial lens. This value is inputted into the box for a fourth lens of the distance vision lens layout power input section 2 in FIG. 2. Besides, the near refraction optometry value is S at +6.50 D, and there is only one trial lens. This value is inputted into the box for a fourth lens of the near vision lens layout power input section 9 in FIG. 2.

Figure 16:
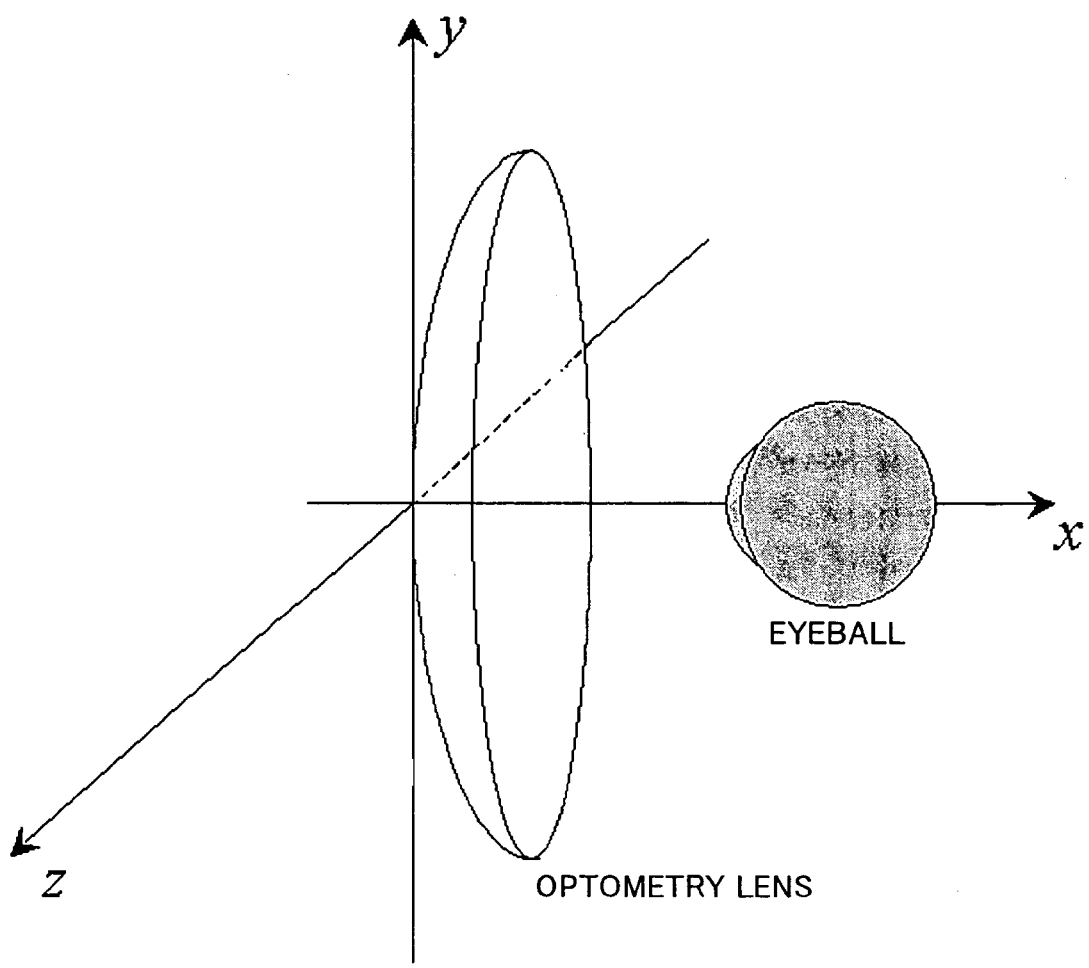
FIG. 16 is xyz coordinates of a trial lens and an eye.

In this case, for the distance vision power optometry, the position of a passing point of a principal ray on the front surface of the fourth lens is at Y=0 mm and z=0 mm which are inputted into the distance vision lens principal ray passing point input section 5, and, for the near vision power optometry, the position of a passing point of a principal ray on the front surface of the fourth lens is at Y=−8 mm and z=0 mm which are inputted into the near vision lens principal ray passing point input section 12. It should be noted that, as for the xyz coordinate system in FIG. 16, y represents a vertical position, and z represents a lateral position. At the time of near vision power optometry, it is necessary to designate a near point distance. The near point distance is 0.35 m in the example shown in FIG. 2.

The shape of the wavefront entering an eye found from the result of the ray tracing can be expressed by the S power, C power, and C axial angle similarly to the lens prescription. However, it is necessary to designate which position the surface wave is at because the shape changes with progression of the wavefront. In conformity to custom of the technical fields of spectacle lens, the position on the rear vertex sphere of a spectacle lens (a sphere with the center of rotation as its center and the distance from the rear vertex of a lens to the center of rotation as its radius) is defined here as a wavefront measurement position. However, it is also conceivable to employ the position on the corneal vertex sphere (a sphere with the center of rotation as its center and the distance from the corneal vertex to the center of rotation as its radius) for the purpose of comparison or the like between lenses or between the lens and a contact lens.

The prescription data of a progressive-addition lens obtained from the optometry includes S at +4.00 D and ADD at 2.50 D, and only these prescription powers are reported from an ophthalmologist or an optician in the conventional order method. Actually, a lens suitable for an eye of a patient is one capable of creating a wavefront with S at +4.00 D at the position on the rear vertex sphere when he or she views a far point, obtained from the far ray tracing result output section 7 in FIG. 2, and capable of creating a wavefront with S at +3.48 D, C at −0.04 D, and Ax at 90° when he or she views an object at a near point of 350 mm, obtained from the near ray tracing result output section 14. These are regarded as the distance vision target values and the near vision target values in the table shown in the embodiment 1 in FIG. 17.

A lens designed based on the wavefront data will be described.

The lens is constituted of a front surface being a progressive surface and a rear surface being a sphere. FIG. 3 shows an astigmatism distribution and an average power (that means an average power error and is also called a power error here) distribution of the progressive surface that is the front surface of this progressive-addition lens. Note that the contour interval in each drawing is 0.25 D pitch, and, in the astigmatism distribution diagram, the amount of astigmatism increases from the central portion (principal meridian) to the peripheral portion. This lens has values, that is, a front surface Actual curve of 6.88 D, a rear surface curve of 3.00 D, a refractive index of 1.70, and a wall thickness of 4.3 mm. The distance vision power measured by placing a lens meter on the rear surface at a position of y=8 mm and z=0 mm (distance portion refractive power measurement position) are S at +3.86 D, C at −0.00 D, and Ax at 85°.

Figure 13:
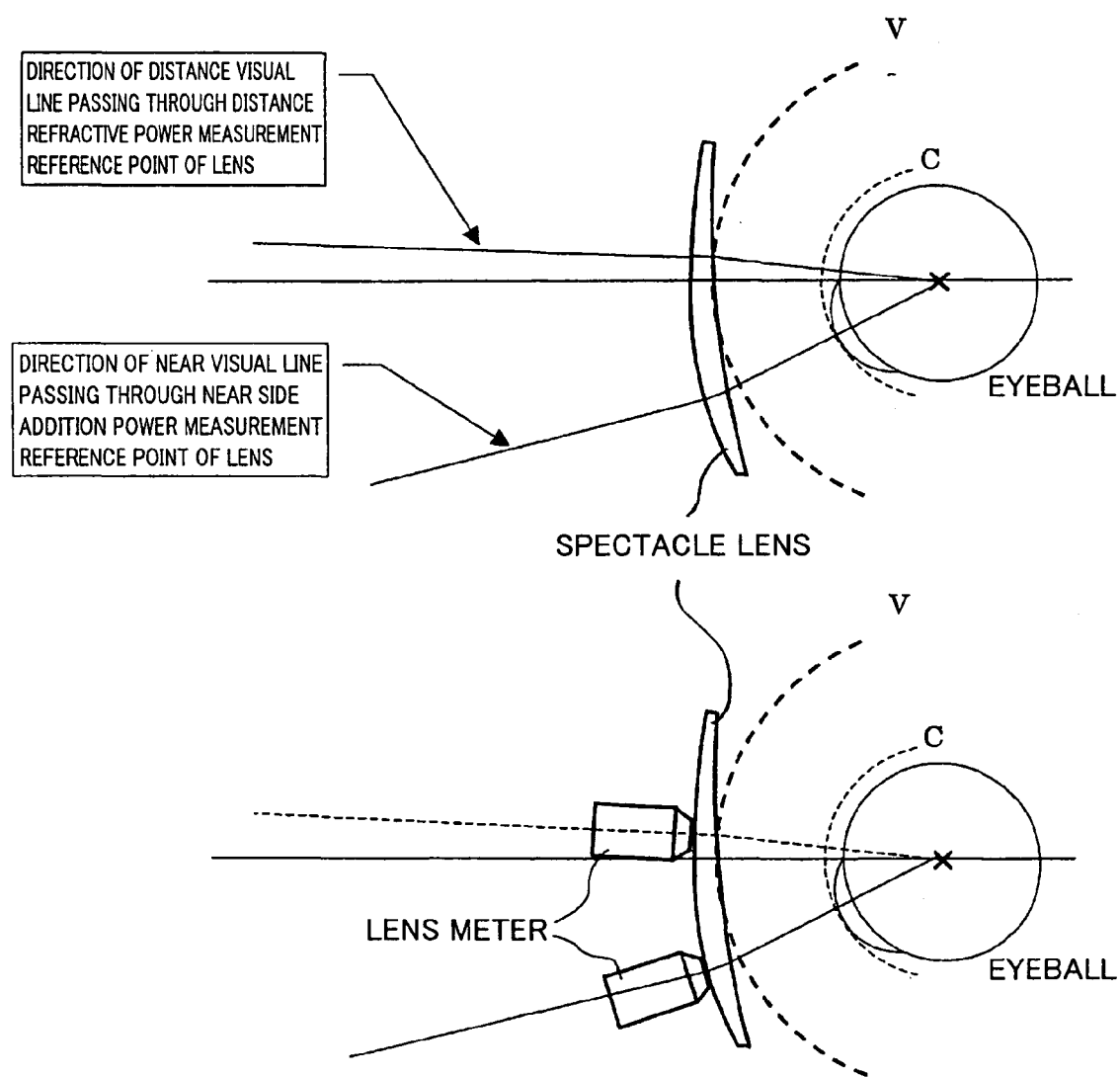
FIG. 13 is a view showing a state of measuring an addition power by placing a lens meter on a progressive surface being a front surface of a progressive-addition lens.

FIG. 13 is an explanatory view of an optical system of measurement by the lens meter. As shown in FIG. 13, the power measured by placing the lens meter on the front surface at a position of y=8 mm and z=0 mm (distance portion measurement position) are S at +3.74 D, C at −0.04 D, and Ax at 0°, the average power being 3.72 D. Note that the average power is obtained by S+C/2. As shown in FIG. 13, the power measured by placing the lens meter on the front surface at a position of y=−14.0 mm and z=2.6 mm (near portion measurement position) are S at +5.66 D, C at −0.14 D, and Ax at 106°, the average power being 5.60 D. The difference in the average power is 1.88 D. In other words, this lens is a prescription lens with S at +3.86 D and ADD at 1.88 D.

The calculation of wavefront s shows that, as the result of the distance vision design, a wavefront created at the rear vertex sphere position by a plane wavefront emitted from an infinite far object, along a ray passing through the position on the front surface at y =8 mm and z =0 mm, has S at +4.14 D, C at −0.29D, and AX at 90°, the average power being +4.00 D, and, as the result of the near vision design, a wavefront created at the rear vertex sphere position by a spherical wavefront emitted from an object at a near point of 350 mm, along a ray passing through the position on the front surface at y =−14.0 mm and z =2.7 mm, has S at +3.91 D, C at −0.90 D, and AX at 104°, the average power being +3.46 D.

As seen from the embodiment 1 in FIG. 17 in which the above-described target values, design results, and average power are summarized, both the far wavefront and near wavefront nearly coincide with the wavefront s at the time of optometry. The manufacturing and placing an order for a spectacle lens are performed using the power data of the design results shown in this table.

Into the near vision lens principal ray passing point input section 12 in FIG. 2 of the embodiment 1, y=0 mm and z=0 mm as the position of a passing point of the principal ray on the front surface of the fourth lens are inputted for the near vision power optometry so as to make the position common with the position of the passing point of the principal ray for the distance vision power optometry. This enables near vision in substantially the same direction as that of a distance visual line. This is the above-described "distance vision/near vision lens power difference mode by a refractor head", corresponding to the third method for determining the addition power to a progressive-addition lens. In this case, it is also possible to find the wavefront entering an eye by performing ray tracing with a computer as in the foregoing, but a resulting lens becomes a spectacle lens with a narrow visual field, failing to function as a progressive-addition lens, and therefore the description thereof is omitted here.

Embodiment 2

Figure 4:
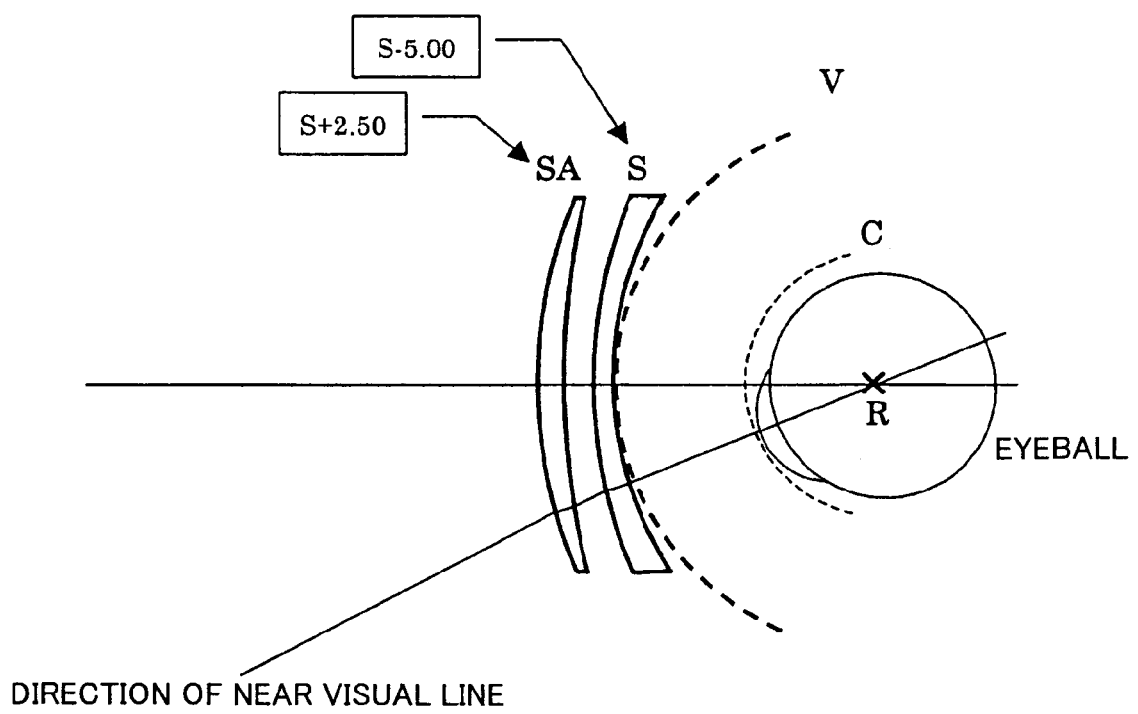
FIG. 4 is an optical path diagram at the time of optometry according to an embodiment 2.
Figure 6:
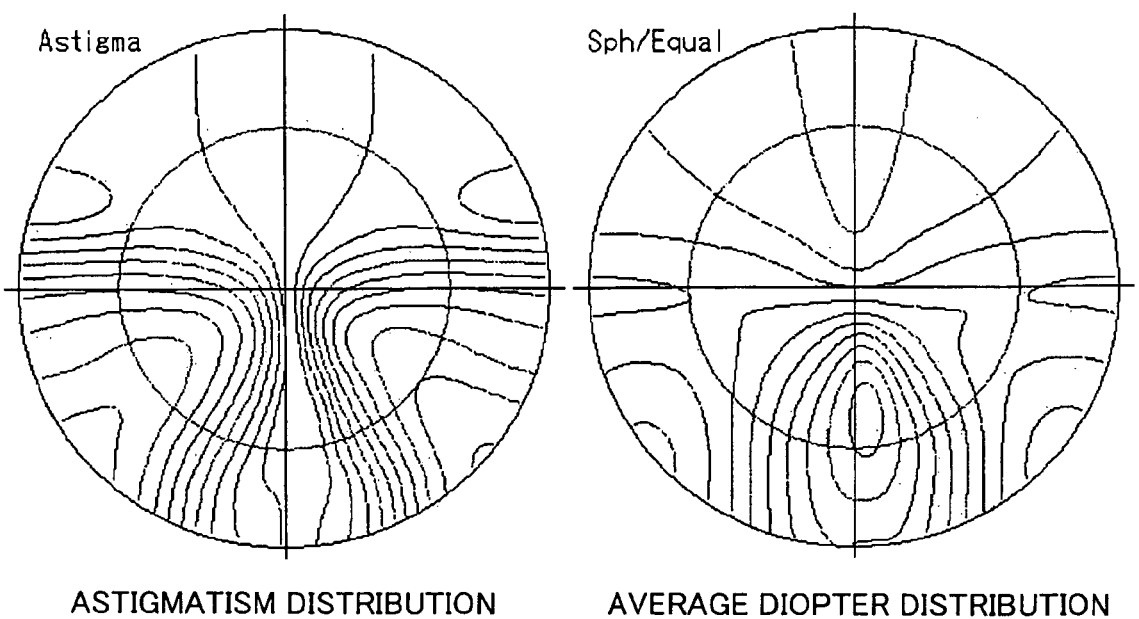
FIG. 6 is an astigmatism distribution diagram and a diagram showing an average power of a spectacle lens with determined optical values.

FIG. 4 is an optical path diagram at the time of optometry according to an embodiment 2, FIG. 5 is an interface screen for finding a wavefront entering an eye by performing ray tracing with a computer, FIG. 6 is an astigmatism distribution diagram and a diagram showing an average power of a spectacle lens with determined optical values, and FIG. 18 for the embodiment 2 is a table in which input and output data are summarized. Referring to these drawings, a spectacle lens optical value determining method, a spectacle lens manufacturing method, and a spectacle lens, and an order placing/receiving system thereof, which are according to the embodiment 2, will be described below. It should be noted that this embodiment is the above-described "near vision lens addition mode", corresponding to the first method for determining an addition power of a progressive-addition lens.

In the example shown in FIG. 5 in this embodiment, the distance refraction optometry value is S at −5.00 D, and there is only one trial lens. This value is inputted into the box for a fourth lens of a distance vision lens layout power input section 2 in FIG. 5. The near refraction optometry value is S at −2.50 D, and there are two trial lenses with S at −5.00 D and S at +2.50 D. These values are inputted such that S at −5.00 D is inputted, similarly to the distance refraction optometry value, into the box for a fourth lens of a near vision lens layout power input section 9 in FIG. 5, and S at +2.50 D is inputted into the box for a third lens.

The prescription data of a progressive-addition lens obtained from the optometry includes S at −5.00 D and ADD at 2.50 D, and only these prescription power are reported from an ophthalmologist or an optician in the conventional order method. Actually, a lens suitable for an eye of a patient is one capable of creating a wavefront with S at −5.00 D at the rear vertex sphere position when he or she views a far point, obtained from a far ray tracing result output section 7 in FIG. 5, and capable of creating a wavefront with S at −5.41 D, C at −0.02 D, and Ax at 180° when he or she views an object at a near point of 350 mm, obtained from a near ray tracing result output section 14. These are regarded as the distance vision target values and the near vision target values in the table shown in the embodiment 2 in FIG. 18.

A lens designed based on the wavefront data will be described. The lens is constituted of a front surface being a progressive surface and a rear surface being a sphere. FIG. 6 shows an astigmatism distribution and an average power distribution of the progressive surface that is the front surface of this progressive-addition lens. Note that the display method is the same as that of FIG. 3. This lens has values, that is, a front surface Actual curve of 3.99 D, a rear surface curve of 9.00 D, a refractive index of 1.70, and a wall thickness of 1.0 mm.

The distance vision power measured by placing a lens meter on the rear surface at a position of y=8 mm and z=0 mm (distance portion refractive power measurement position) are S at −4.82 D, C at −0.00 D, and Ax at 132°. The power measured by placing the lens meter on the front surface at a position of y=8 mm and z=0 mm (distance portion measurement position) are S at −4.80 D, C at −0.02 D, and Ax at 180°, the average power being −4.81 D.

Further, the power measured by placing the lens meter on the front surface at a position of y=−14.0 mm and z=2.1 mm (near portion measurement position) are S at −2.56 D, C at −0.10 D, and Ax at 112°, the average power being −2.61 D. The difference in the average power is 2.20 D. In other words, this lens is a prescription lens with S at −4.82 D and ADD at 2.20 D.

The calculation of wavefront s shows that, as the result of the distance vision design, a wavefront created on the rear vertex sphere position by a plane wavefront emitted from an infinite far object, along a ray passing through the position on the front surface at y=8 mm and z=0 mm, has S at −4.85 D, C at −0.30 D, and AX at 180°, and, as the result of the near vision design, a wavefront created on the rear vertex sphere position by a spherical wavefront emitted from an object at a near point of 350 mm, along a ray passing through the position on the front surface at y=−14.0 mm and z=2.1 mm, has S at −5.38 D, C at −0.10 D, and AX at 100°.

As seen from the embodiment 2 in FIG. 18 in which the above-described target values, design results, and average power are summarized, both the far wavefront and near wavefront nearly coincide with the wavefronts at the time of optometry. The manufacturing and placing an order for a spectacle lens are performed using the power data of the design results shown in this table.

Embodiment 3

Figure 7A:
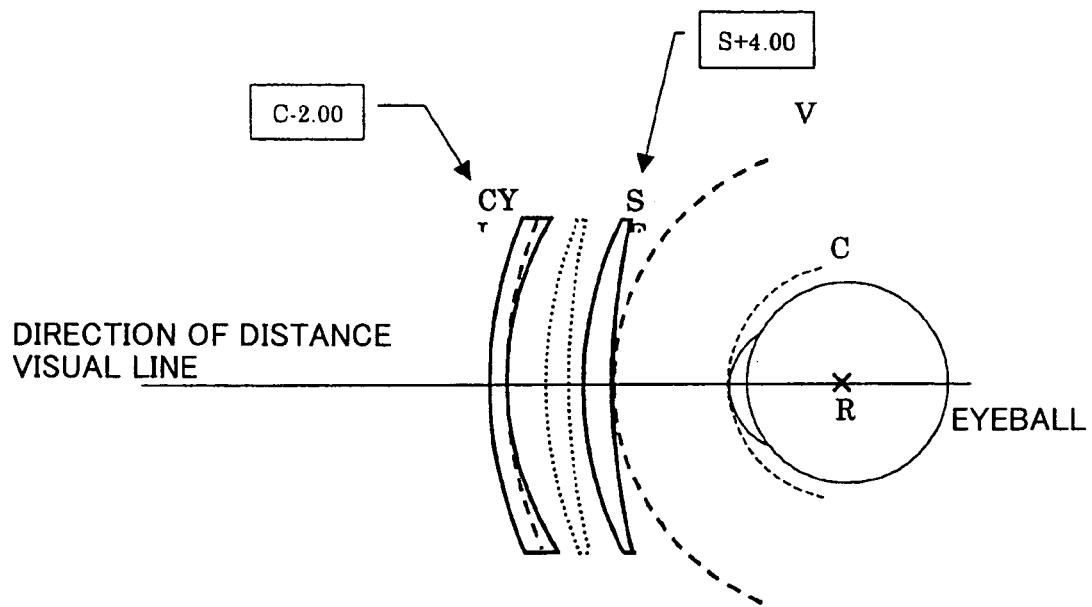
FIG. 7(a) is a diagram of an optical path in a direction of a distance visual line.
Figure 7B:
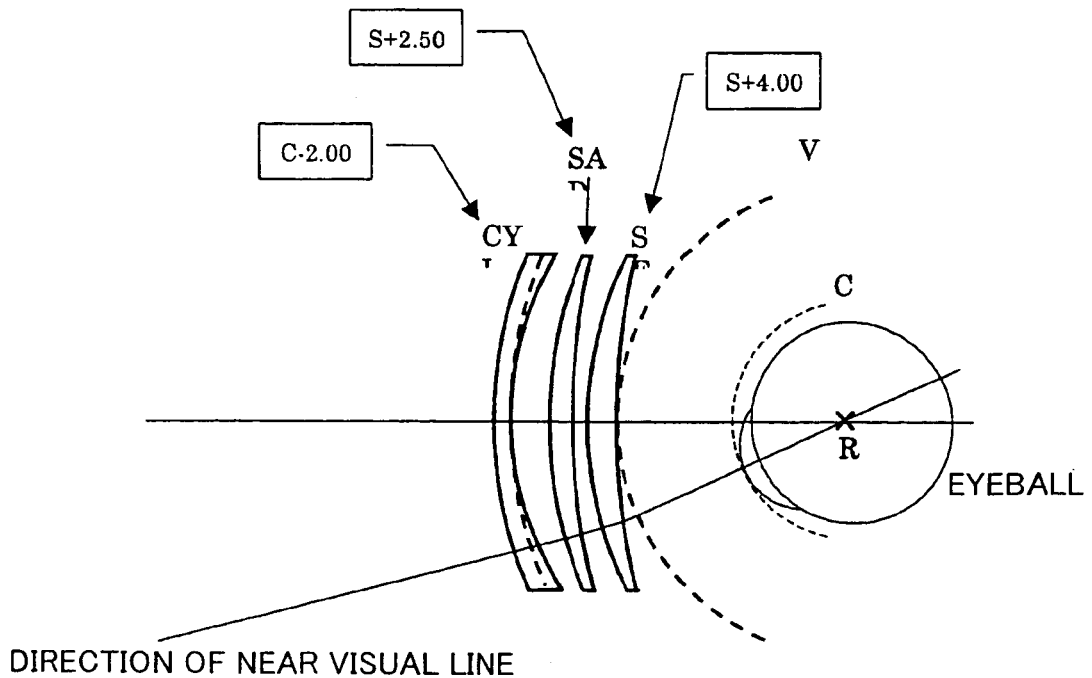
FIG. 7(b) is a diagram of an optical path in a direction of a near visual line.
Figure 9:
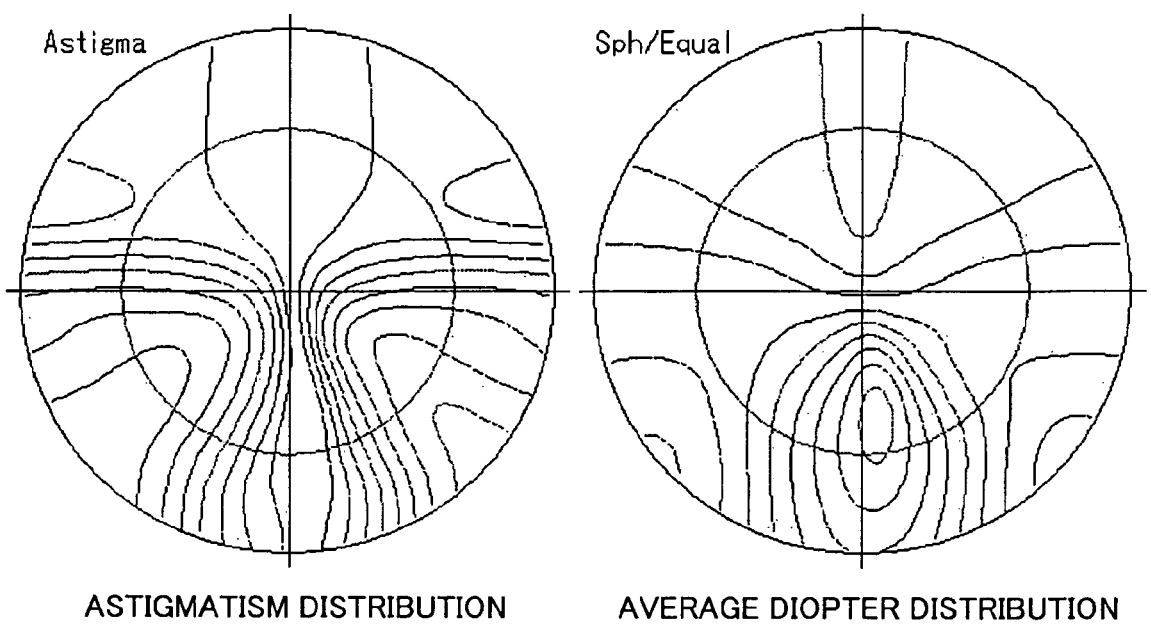
FIG. 9 is an astigmatism distribution diagram and a diagram showing an average power of a spectacle lens with determined optical values.

FIG. 7 is an optical path diagram at the time of optometry according to an embodiment 3, in which FIG. 7(*a*) is a diagram of an optical path in a direction of a distance visual line, and FIG. 7(*b*) is a diagram of an optical path in a direction of a near visual line, FIG. 8 is an interface screen for finding a wavefront entering an eye by performing ray tracing with a computer, FIG. 9 is an astigmatism distribution diagram and a diagram showing an average power of a spectacle lens with determined optical values, and FIG. 19 for the embodiment 3 is a table in which input and output data are summarized. Referring to these drawings, a spectacle lens optical value determining method, a spectacle lens manufacturing method, a spectacle lens, and an order placing/receiving system thereof, which are according to the embodiment 3, will be described below. It should be noted that this embodiment is the above-described "near vision lens addition mode", corresponding to the first method for determining the addition power of a progressive-addition lens.

In the example shown in FIG. 8 in this embodiment, the distance refraction optometry values are S at +4.00 D, C at −2.00 D, and AX at 30°, and there are two trial lenses with S at +4.00 D and C at −2.00 D. These values are inputted such that S at +4.00 D is inputted into the box for a fourth lens of a distance vision lens layout power input section 2 in FIG. 8, and C at −2.00 D is inputted into the box for a second lens. The near vision trial lens has a configuration made by adding one lens with S at +2.50 D to the trial lens for distance refraction. These values are inputted such that S at +4.00 D and C at −2.00 D are respectively inputted into the box for a fourth lens and the box for a second lens of a near vision lens layout power input section 9 in FIG. 8, similarly to the distance refraction optometry values, and further S at +2.50 D is inputted into the box for a third lens.

The prescription data of a progressive-addition lens obtained from the optometry includes S at +4.00 D, C at −2.00 D, AX at 30°, and ADD at 2.50 D, and only these prescription power are reported from an ophthalmologist or an optician in the conventional order method. Actually, a lens suitable for an eye of a patient is one capable of creating a wavefront with S at +4.00 D, C at −2.03 D, and AX at 30° at the rear vertex sphere position when he or she views a far point, obtained from a far ray tracing result output section 7 in FIG. 8, and capable of creating a wavefront with S at +3.50 D, C at −2.01 D, and Ax at 30.5° when he or she views an object at a near point of 350 mm, obtained from a near ray tracing result output section 14. These are regarded as the distance vision target values and the near vision target values in the table shown in the embodiment 3 in FIG. 19.

A lens designed based on the wavefront data will be described. The lens is constituted of a front surface being a progressive surface and a rear surface being a toric surface. FIG. 9 shows an astigmatism distribution and an average power distribution of the progressive surface that is the front surface of this progressive-addition lens. Note that the display method is the same as that of FIG. 3. The front surface Actual curve is 6.88 D, the rear surface has a curve in an S direction of 3.00 D and a curve in a C direction of 5.00 D, the refractive index is 1.70, and the wall thickness is 4.5 mm. The distance vision power measured by placing a lens meter on the rear surface at a position of y=8 mm and z=0 mm (distance portion refractive power measurement position) are S at +3.96 D, C at −2.00 D, and Ax at 26°.

The power measured by placing the lens meter on the front surface at a position of y =8mm and z =0mm (distance portion measurement position) are S at +3.83D, C at −1.97D, and Ax at 30°, the average power being +2.85D. The power measured by placing the lens meter on the front surface at a position of y =−14.0 mm and z =2.1 mm (near portion measurement position) are S at +5.67D, C at −1 .76D, and Ax at 27°, the average power being 4.79D. The difference in the average power is 1 .94D. In other words, this lens is a prescription lens with S at +3.96D, C at +2.00 D, Ax at 26° D, and ADD at 1.94D.

The calculation of wavefronts shows that, as the result of the distance vision design, a wavefront created on the rear vertex sphere position by a plane wavefront emitted from an infinite far object, along a ray passing through the position on the front surface at y=8 mm and z=0 mm, has S at +4.05 D, C at −2.10 D, and AX at 30°, and, as the result of the near vision design, a wavefront created on the rear vertex sphere position by a spherical wavefront emitted from an object at a near point of 350 mm, along a ray passing through the position on the front surface at y=−14.0 mm and z=2.1 mm, has S at +3.29 D, C at −1.58 D, and Ax at 33.0°.

As seen from the embodiment 3 in FIG. 19 in which the above-described target values, design results, and average power are summarized, both the far wavefront and near wavefront nearly coincide with the wavefront s at the time of optometry. The manufacturing and placing an order for a spectacle lens are performed using the power data of the design results shown in this table.

Embodiment 4

Figure 10:
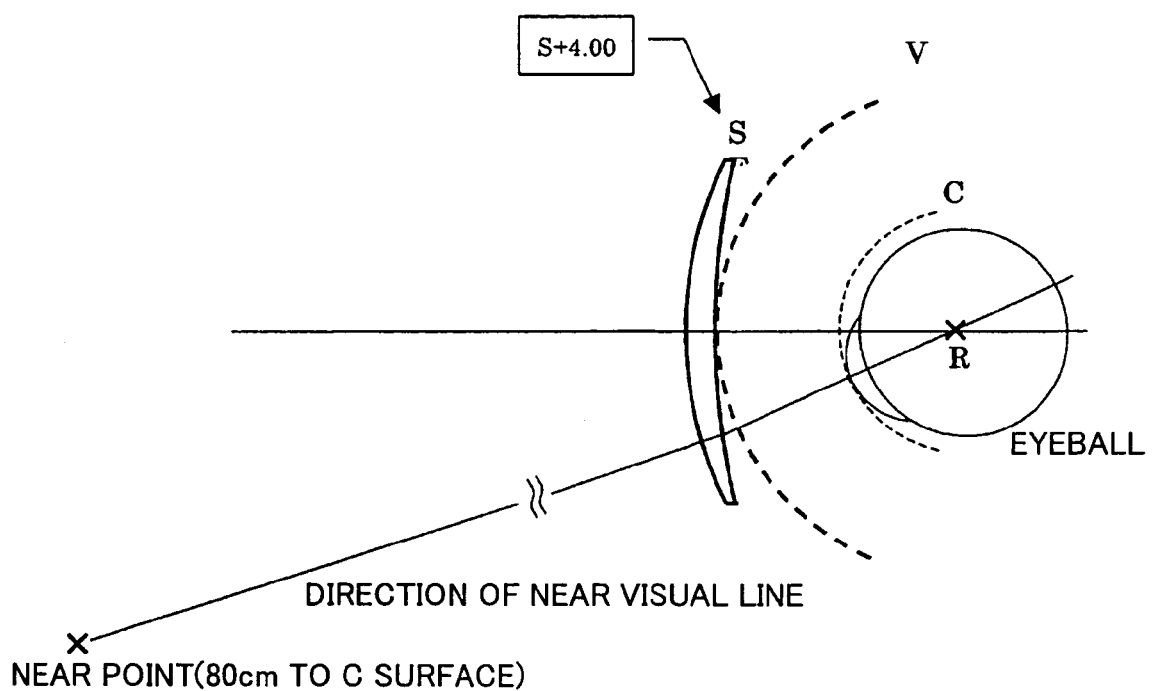
FIG. 10 is an optical path diagram at the time of optometry of a spectacle lens according to an embodiment 4.
Figure 12:
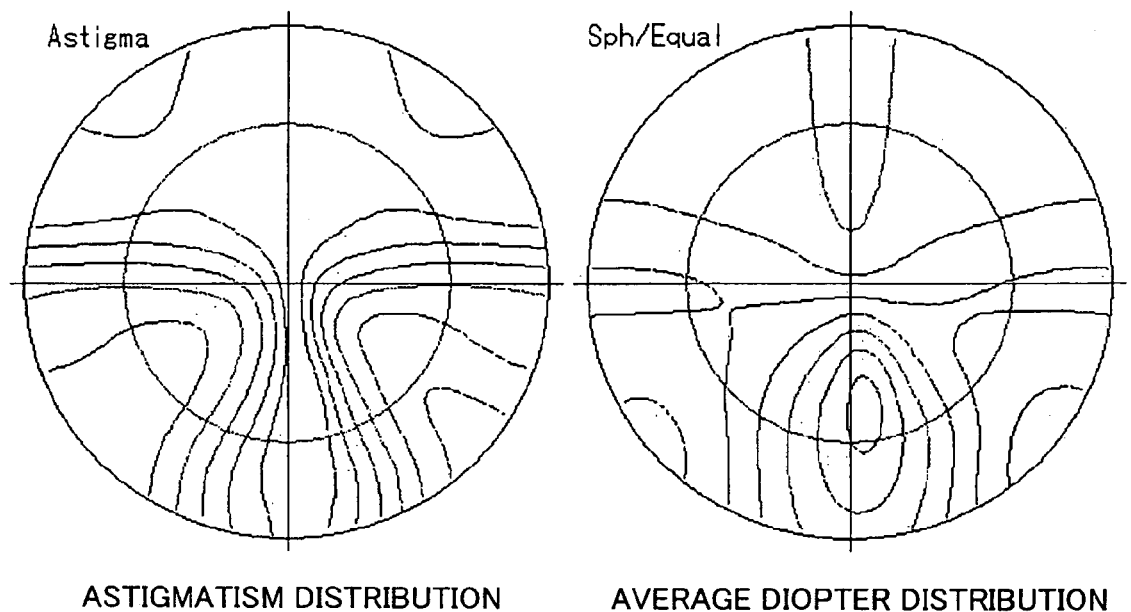
FIG. 12 is an astigmatism distribution diagram and a diagram showing an average power of a spectacle lens with determined optical values.

FIG. 10 is an optical path diagram at the time of optometry according to an embodiment 4, FIG. 11 is an interface screen for finding a wavefront entering an eye by performing ray tracing with a computer, FIG. 12 is an astigmatism distribution diagram and a diagram showing an average power of a spectacle lens with determined optical values, and FIG. 20 for the embodiment 4 is a table in which input and output data are summarized. Referring to these drawings, a spectacle lens optical value determining method, a spectacle lens manufacturing method, a spectacle lens, and an order placing/receiving system thereof, which are according to the embodiment 4, will be described below. It should be noted that this embodiment is the above-described "mode with a complementary refractive power as an addition power", corresponding to the fourth method for determining the addition power of a progressive-addition lens.

In the example shown in FIG. 11 in this embodiment, the distance refraction optometry value is S at +4.00 D, and there is only one trial lens. This value S at +4.00 D is inputted into the box for a fourth lens of a distance vision lens layout power input section 2 in FIG. 11. The near refraction value should be found not by using trial lens but by measuring the distance of a near point of accommodation, still using the distance trial lens. Therefore, S at +4.00 D, the same as the distance refraction optometry value, is inputted also into the box for a fourth lens of a near vision lens layout power input section 9 in FIG. 11. In this case, the distance of a near point of accommodation (distance from the corneal) is 1000 mm, which is inputted into the box for the near distance at 12 in FIG. 11. As obtained from a near ray tracing result output section 14 in FIG. 11, a wavefront at the rear vertex when one views an object point at a near point distance has S at +3.03 D and C at −0.08 D. When the near point distance is brought to 350 mm by adding an addition power, the nominal addition power is (1/0.35 m−1/1 m), which is about 1.86 D.

The prescription data of a progressive-addition lens obtained from the optometry includes S at +4.00 D and ADD at 1.86 D, but the addition power are normally manufactured every 0.25 D pitch, so that ADD in this case is rounded to 1.75 D or 2.00 D. Only these prescription power are reported from an ophthalmologist or an optician in the conventional order method. Actually, a lens suitable for an eye of a patient is one capable of creating a wavefront with S at +4.00D at the rear vertex sphere position when he or she views a far point, obtained from the output result in FIG. 11, and capable of creating a wavefront with S at +3.03 D and C at −0.08 D when he or she views an object at a near point of 350 mm. These are regarded as the distance vision target values and the near vision target values in the table shown in the embodiment 4 in FIG. 20.

A lens designed based on the wavefront data will be described. The lens is constituted of a front surface being a progressive surface and a rear surface being a sphere. FIG. 12 shows an astigmatism distribution and an average power distribution of the progressive surface that is the front surface of this progressive-addition lens. Note that the display method is the same as that of FIG. 3. This lens has values, that is, a front surface Actual curve of 7.09 D, a rear surface curve of 3.20 D, a refractive index of 1.70, and a wall thickness of 1.0 mm. The distance vision power measured by placing a lens meter on the rear surface at a position of y=8 mm and z=0 mm (distance portion refractive power measurement position) are S at +3.85 D, C at −0.00 D, and Ax at 89°.

The power measured by placing the lens meter on the front surface at a position of y=8 mm and z=0 mm (distance portion measurement position) are S at +3.73 D, C at −0.03 D, and Ax at 0°, the average power being +3.71 D. The power measured by placing the lens meter on the front surface at a position of y=−14.0 mm and z=2.1 mm (near portion measurement position) are S at +5.25 D, C at −0.12 D, and Ax at 106°, the average power being +5.19 D. The difference in the average power is 1.48 D. In other words, this lens is a prescription lens with S at +3.73 D, C at −0.03 D, Ax at 0°, and ADD at 1.48 D.

The calculation of wavefronts shows that, as the result of the distance vision design, a wavefront created on the rear vertex sphere position by a plane wavefront emitted from an infinite far object, along a ray passing through the position on the front surface at y=8 mm and z=0 mm, has S at +4.15 D, C at −0.30 D, and AX at 90°, and, as the result of the near vision design, a wavefront created on the rear vertex sphere position by a spherical wavefront emitted from an object at a near point of 350 mm, along a ray passing through the position on the front surface at y=−14.0 mm and z=2.1 mm, has S at +3.41 D, C at −0.83 D, and AX at 103°.

As seen from the embodiment 4 in FIG. 20 in which the above-described target values, design results, and average power are summarized, both the far wavefront and near wavefront nearly coincide with the wavefronts at the time of optometry. The manufacturing and placing an order for a spectacle lens are performed using the power data of the design results shown in this table.

It should be noted that all trial lenses and eyeglass test frames used for the subjective optometry by the lens exchange method are sometimes not exactly equivalent in practice, and they may be slightly different in specifications among manufacturers. The trial lenses may be different in lens curve or wall thickness at the lens center although they are the same in refractive power of lens, or they may be different in refraction index of the lens material depending on the refractive power. Besides, the eyeglass test frames may have variations in space between mounting positions of trial lenses, for example, 3.5 mm to 6 mm, among manufactures.

Accordingly, accurate calculation of the state of a wavefront at the time of optometry requires information such as the specifications of these trial lenses and the value of the space between the lens mounting positions in an eyeglass test frame, what refractive power of trial lens is mounted on which mounting position of the eyeglass test frame, the distance between the trial lens closest to an eyeball and the corneal vertex, and so on.

Besides, if it is anticipated that the distance between a spectacle lens and the corneal of a patient when he or she wears finished spectacles with ordered lenses being inserted into an eyeglass frame is different from the distance between the trial lens and the corneal at the time of optometry, the expected distance between the spectacle lens and the corneal of the patient at the time of wearing the spectacles is also necessary information for the accurate calculation of the state of the wavefront at the time of optometry.

However, every recent trial lens has a meniscus shape. In addition, the refractive power of trial lens used in determining the addition power is relatively weak, mainly ranging from 1.00 D to 3.00 D. From these facts, when precise information such as the space between the mounting positions of trial lenses in an eyeglass test frame, the mounting position of the trial lens, the shape of the trial lens cannot be obtained in practice, calculation of the wavefront at the time of optometry through use of standard values is also effective means in business.

Table 1 in FIG. 14 shows convex surface shapes as standard shapes of the trial lenses, center wall thicknesses, and refractive indexes as examples of standard values, with the standard value of the space between the mounting positions of trial lenses in an eyeglass test frame being 4 mm, and the distance between the trial lens closest to an eyeball and the corneal vertex and the distance between a spectacle lens and the corneal of a patient when he or she wears finished spectacles with ordered progressive-addition lenses being inserted in an eyeglass frame being 12 mm. More specifically, it is more preferable to calculate the wavefront at the time of optometry, even when using standard values, and to provide the addition power to a progressive-addition lens based on the calculation result than to provide the addition power to a progressive-addition lens without identification of the optometry method as in the prior art.

Beside, even if the order information of a progressive-addition lens actually includes no information on the optometry method, the same effect can be attained even by a method of providing specifications how to provide the addition power in the order information because the wavefront can be calculated as long as a plurality of specifications on the way to provide the addition power to a progressive-addition lens are prepared such that the respective specifications correspond to the optometry method using standard values.

Although each of the above-described embodiments takes a case, as an example, in which the spectacle lens is a progressive-addition lens, other kinds of lenses are also adoptable.

Figure 24:
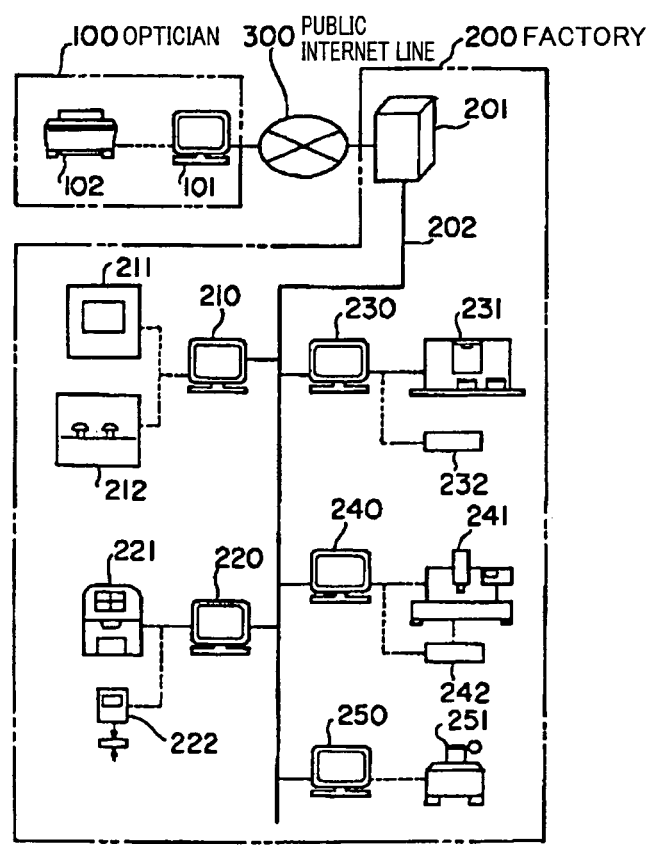
FIG. 24 is a diagram showing the entire configuration of an order placing/receiving system of the present invention.

Next, as an order placing/receiving system, a conceivable configuration is, for example, an order placing/receiving system shown in FIG. 24. More specifically, the order placing/receiving system comprises a terminal unit 101 located on an orderer side of a spectacle lens (optician 100), and a processing unit 201 located on a processor side of the spectacle lens (spectacle lens manufacturer 200) connected to the terminal unit 101 via a public communication line 300 (including an indirect method using a server or the like). In this system, an order is placed by transmitting, to the processing unit 201 on the processor side of the spectacle lens via the terminal unit 101 on the orderer side, spectacle lens information, eyeglass frame information, prescription values including identification information of an addition power determining method, that is, what method has been used for determining the prescription power and addition power at the time of optometry, layout information, and design and/or processing condition data information selected, when required, from among information including processing designation information. It is preferable to use, for example, the interface screen in FIG. 2 as an input means of the above-described prescription values including the identification information of the addition power determining method at the time of optometry. The spectacle lens processor side regards, as reception of an order, the fact that the processing unit receives the prescription values including the identification information of the addition power determining method.

Next, the following method is conceivable as a manufacturing method. Namely, a spectacle lens is designed by finding a practical appropriate value of the addition power to be actually provided to a progressive-addition lens based on the information including identification information of the addition power determining method, that is, what method has been used for determining the prescription power and addition power at the time of optometry, which is transmitted to the processing unit located on the spectacle lens processor side. Then, lens processing is performed such that a lens blank is selected, cut by an NC cutting machine, and polished based on a processing instruction at a manufacturing site. When surface treatments (abrasion-resistant hard coating formation, anti-reflection film formation, lens dyeing, water repellent treatment, ultraviolet cutting film formation, anti-fogging treatment, and so on) are necessary, the treatments are also performed here. As a result, a prescription lens in a circular shape is completed. Next, the circular shaped lens is subjected to beveling or smoothing at the periphery based on spectacle layout information, in correspondence with a predetermined edge shape. The beveling or smoothing is performed at a machining center. This processing is performed, for example, by a tool and a processing method described in Japanese Unexamined Utility Model Publication No. Hei 6-17853 and Japanese Unexamined Patent Publication No. Hei 6-34923 which are proposed by the present applicant.

As shown in these publications, selection of the kind of glass material (glass, plastic, polycarbonate, acryl, or the like), selection of the frame material, input of the frame PD (FPD, DBL), input of PD (binocular, monocular), input of lateral decentration amount X, input of vertical decentration amount Y, input of cylindrical axis, input of finished size, designation of bevel form, and so on, are used as processing conditions, so that these input data are automatically introduced by a program at the time of setting a processing mode of a processing apparatus. When these predetermined items are set and a start switch is pressed, periphery processing is automatically performed. In this way, a lens with a beveled or smoothed periphery is manufactured and shipped from a factory after an inspection process to the spectacle lens orderer side. On the spectacle lens orderer side, this processed lens is mounted on a selected eyeglass frame for assembly. Although an aspect in which beveling or smoothing of the periphery is performed by the manufacturer is described in this embodiment, this processing may be performed on the spectacle lens orderer side.

Figure 25:
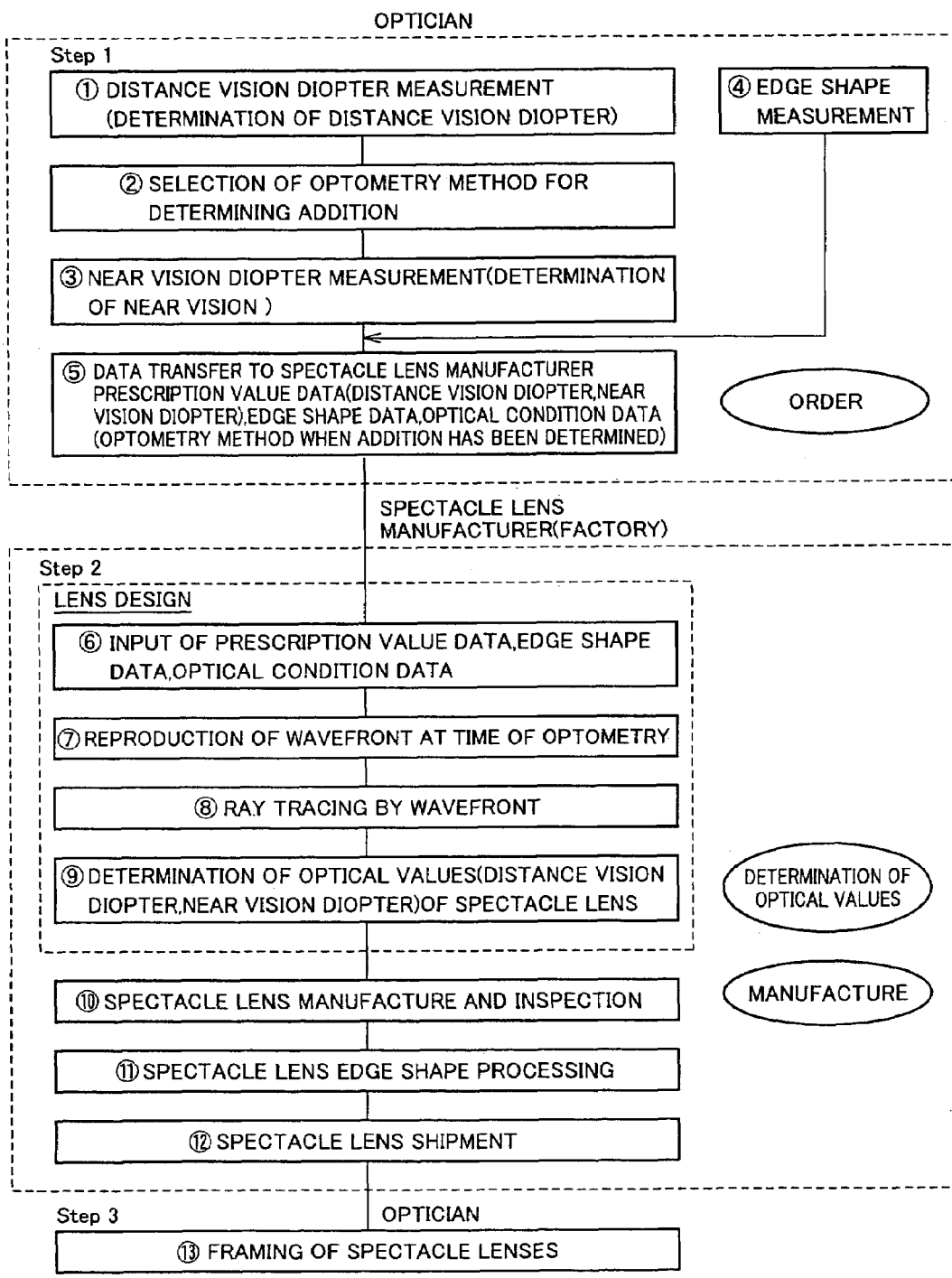
FIG. 25 is a flowchart showing procedures for embodying the present invention.

A flowchart for embodying the present invention is shown in FIG. 25 and will be described.

Step 1 Work of optometry of a subject and ordering work at an optician
① Perform distance vision power measurement to determine a distance vision power.
② Select an optometry method for determining the addition power.
③ Perform near vision power measurement by the selected optometry method to determine a near vision.
④ Measure the edge shape of a frame or a pattern.
⑤ Place an order by performing data transfer to a spectacle lens manufacturer prescription value data (distance vision power, near vision power), edge shape data, optical condition data (optometry method when the addition power has been determined).

Step 2 Lens design, lens manufacture, edge shape processing, and inspection and shipping work at the spectacle lens manufacturer
⑥ Input the prescription value data, edge shape data, and optical condition data transferred from the optician.
⑦ Reproduce the wavefront at the time of optometry.
⑧ Perform ray tracing by the wavefront.
⑨ Determine optical values (distance vision power, near vision power) of a spectacle lens.
⑩ Manufacture and inspect a spectacle lens with the determined optical values.
⑪ Perform edge shape processing for the spectacle lens.
⑫ Ship a spectacle lens finished product to the optician.

Step 3 Assembly work for a spectacle finished product at the optician
⑬ Complete spectacles by framing spectacle lenses sent to the optician into a frame or pattern.

INDUSTRIAL AVAILABILITY

As has been described, the present invention is characterized in that an optical value of a spectacle lens is selected and determined so that a wavefront entering an eye of a subject at the time of optometry and a wavefront entering the eye when the subject wears the spectacle lens and views an object coincide with or are approximate to each other. This enables minimization of "sway" and "distortion" that one feels when wearing spectacles.

The invention claimed is:
1. A spectacle lens optical value determining method for determining an optical value including a refractive power of a spectacle lens suitable for a subject based on at least a prescription value including a refractive power data obtained from optometry using a trial lens, wherein the optical value of the spectacle lens is selected and determined so that a wavefront entering an eye of the subject at the time of optometry and a wavefront entering the eye when the subject wears the spectacle lens and views an object coincide with or are approximate to each other.

2. The spectacle lens optical value determining method according to claim 1,
wherein the spectacle lens is a progressive-addition lens, and the optical value is an optical value including an addition power.

3. The spectacle lens optical value determining method according to claim 1,
wherein the wavefront entering the eye of the subject at the time of optometry is found through use of a ray tracing method based on optical conditions specific to an optometry method used at the time of optometry.

4. A spectacle lens manufacturing method wherein a spectacle lens is manufactured based on an optical value which has been determined using the spectacle lens optical value determining method according to claim 1.

5. A spectacle lens manufactured by the spectacle lens manufacturing method according to claim 4.

6. A spectacle lens order placing and receiving system for placing and receiving an order for a spectacle lens by sending to a manufacturer order information including at least the prescription value including the refractive power data obtained from optometry using the trial lens, wherein the order information includes optical condition information of an optometry method required to obtain a wavefront used in the spectacle lens optical value determining method according to claim 1.

7. The spectacle lens optical value determining method according to claim 2,
wherein the wavefront entering the eye of the subject at the time of optometry is found through use of a ray tracing method based on optical conditions specific to an optometry method used at the time of optometry.

8. A spectacle lens manufacturing method wherein a spectacle lens is manufactured based on an optical value which has been determined using the spectacle lens optical value determining method according to claim 2.

9. A spectacle lens manufacturing method wherein a spectacle lens is manufactured based on an optical value which has been determined using the spectacle lens optical value determining method according to claim 3.

10. A spectacle lens order placing and receiving system for placing and receiving an order for a spectacle lens by sending to a manufacturer order information including at least the prescription value including the refractive power data obtained from optometry using the trial lens, wherein the order information includes optical condition information of an optometry method required to obtain a wavefront used in the spectacle lens optical value determining method according to claim 2.

11. A spectacle lens order placing and receiving system for placing and receiving an order for a spectacle lens by sending to a manufacturer order information including at least the prescription value including the refractive power data obtained from optometry using the trial lens, wherein the order information includes optical condition information of an optometry method required to obtain a wavefront used in the spectacle lens optical value determining method according to claim 3.

12. The spectacle lens optical value determining method according to claim 1,
wherein the optometry using the trial lens is the optometry based on a subjective optometry method by a lens exchange method.

13. The spectacle lens optical value determining method according to claim 12,
wherein the wavefront entering the eye of the subject at the time of optometry is found through use of a ray tracing method based on optical conditions specific to an optometry method used at the time of optometry.

14. The spectacle lens manufacturing method wherein a spectacle lens is manufactured based on an optical value which has been determined using the spectacle lens optical value determining method according to claim 12.

15. The spectacle lens manufacturing method wherein a spectacle lens is manufactured based on an optical value which has been determined using the spectacle lens optical value determining method according to claim 13.

16. The spectacle lens manufactured by the spectacle lens manufacturing method according to claim 14.

17. The spectacle lens manufactured by the spectacle lens manufacturing method according to claim 15.

18. A spectacle lens order placing and receiving system for placing and receiving an order for a spectacle lens by sending to a manufacturer order information including at least the prescription value including refractive power data obtained from optometry using the trial lens, wherein the order information includes optical condition information of an optometry method required to obtain a wavefront used in the spectacle lens optical value determining method according to claim 12.

19. A spectacle lens order placing and receiving system for placing and receiving an order for a spectacle lens by sending to a manufacturer order information including at least the prescription value including refractive power data obtained from optometry using the trial lens, wherein the order information includes optical condition information of an optometry method required to obtain a wavefront used in the spectacle lens optical value determining method according to claim 13.

* * * * *

UNITED STATES PATENT AND TRADEMARK OFFICE
CERTIFICATE OF CORRECTION

| | | |
|---|---|---|
| PATENT NO. | : 7,118,215 B2 | Page 1 of 1 |
| APPLICATION NO. | : 10/486720 | |
| DATED | : October 10, 2006 | |
| INVENTOR(S) | : Hua Ql and Takashi Hatanaka | |

It is certified that error appears in the above-identified patent and that said Letters Patent is hereby corrected as shown below:

Title Page
Item (54) should read --Spectacle Lens Optical Value Determining Method, Spectacle Lens Manufacturing Method, Spectacle Lens, and Order Placing/Receiving System of the Same--

Signed and Sealed this

Twenty-third Day of January, 2007

JON W. DUDAS
*Director of the United States Patent and Trademark Office*